(12) United States Patent
Belmares et al.

(10) Patent No.: US 7,588,911 B2
(45) Date of Patent: Sep. 15, 2009

(54) ASSAYS FOR DETECTING INHIBITORS OF BINDING BETWEEN COX-2 AND PDZ PROTEINS

(75) Inventors: Michael P. Belmares, San Jose, CA (US); Jonathan David Garman, San Jose, CA (US); Peter S. Lu, Palo Alto, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 284 days.

(21) Appl. No.: 11/426,282

(22) Filed: Jun. 23, 2006

(65) Prior Publication Data

US 2007/0020717 A1 Jan. 25, 2007

Related U.S. Application Data

(60) Provisional application No. 60/693,988, filed on Jun. 23, 2005.

(51) Int. Cl.
C12Q 1/26 (2006.01)
(52) U.S. Cl. ....................................................... 435/25
(58) Field of Classification Search ................ 435/69.2, 435/25
See application file for complete search history.

(56) References Cited

U.S. PATENT DOCUMENTS

2005/0164344 A1* 7/2005 Worley et al. ............... 435/69.1
2008/0227684 A1* 9/2008 Belmares et al. ................ 514/2

FOREIGN PATENT DOCUMENTS

WO WO 2004/045535 A2 6/2004
WO WO 2007/002395 A1 1/2007

OTHER PUBLICATIONS

Iwamoto et al., "Differential modulation of NR1-NR2A and NR1-NR2B subtypes of NMDA receptor by PDZ domain-containing proteins," J. Neurochemistry, 89:100-108 (2004).
Kardosh et al., "Differential Effects of Selective COX-2 Inhibitors on Cell Cycle Regulation and Proliferation of Glioblastoma Cell Lines," Cancer Biology & Therapy, 3(1):55-62 (2004).
Kreienkamp et al., "The Calcium-independent Receptor for α-Latrotoxin from Human and Rodent Brains Interacts with Members of the ProSAP/SSTRIP/Shank Family of Multidomain Proteins," J. Biol. Chem., 275(42):32387-32390 (2000).
Laura et al., "MAGI-1; A Widely Expressed, Alternatively Spliced tight Junction Protein," Experimental Cell Research, 275:155-170 (2002).
Sabio et al., "Stress- and mitogen-induced phosphorylation of the synapse-associated protein SAP90/PSD-95 by activation of SAPK3/p38γ and ERK1/ERK2," Biochem. J., 380:19-30 (2004).
Tang et al., "Flavonoids from Radix scutellariae as potential stroke therapeutic agents by targeting the second postsynaptic density 95 (PSD-95)/disc large/zonula occludens-1 (PDZ) domain of PSD-95," Phytomedicine, 11:277-284 (2004).

Weggen et al., "A subset of NSAIDs lower amyloidogenic Aβ42 independently of cyclooxygenase," Nature, 414:212-216 (2001).
Hewett et al., "Cyclooxygenase-2 contributes to N-methyl-D-aspartate-mediated neuronal cell death in primary cortical cell culture" The Journal of Pharmacology and Experimental Therapeutics, 293(2):417-425 (2000).
Hixson et al., "Antiproliferative effect of NSAIDs against human colon cancer cells," Cancer Epidemiology, Biomarkers and Prevention, 3(5):433-438 (1994).
International Preliminary Examination Report mailed Jul. 04, 2007 for Application PCT/US2003/036698.
International Search Report mailed May 30, 2006 for application PCT/US2003/036698 (WO2004/045535 A3).
International Search Report mailed Nov. 14, 2006 for application PCT/US/06/24475 (WO 2007/002395 A1 ).
Iwamoto et al., "Differential modulation of NR1-NR2A and NR1-NR2B subtypes of NMDA receptor by PDZ domain-containing proteins" J. Neurochem., 89:100-108, (2004).
Jaffrey et al., "Capon: A Protein Associated with Neuronal Nitric Oxide Synthase that Regulates Its interactions with PSD-95", Neuron, 20:115-124, (1998).
Komau et al., "Domain interactions between NMDA receptor subunits and the postsyanptic density protein, PSD-95", Science, 269:1737-1740, (1995).
Kardosh et al., "Differential Effects of Selective COX-2 inhibitors on cell cycle regulation and proliferation of glioblastoma cell lines", Cancer Biol. Ther., 3(1):55-62, (2004).
Kreienkamp et al., "The calcium-independent receptor for alpha-latrotoxin from human and rodent brains interacts with members of the proSAP/SSTRIP/Shank family of multidomain proteins", J. Biol. Chem., 275(42):32387-32390, (2000).
Laura et al., "MAG1-1: a widely expressed, alternatively spliced tight junction protein", Exp. Cell Res., 275:155.170, (2002).
Sabio et al., "Stress and mitogen-induced phosphorylation of the synapse-associated protein SAP90/PSD-95 by activation of SAPK3/p38-gamma and ERK1/ERK2", Biochem J., 380:19-30, (2004).
Saras et al., "PDZ domains bind carboxy-terminal sequences of target proteins," Trends in Biochemical Sciences, 21(12):455-458 (1996).

(Continued)

Primary Examiner—Ralph Gitomer
(74) Attorney, Agent, or Firm—Townsend and Townsend and Crew, LLP

(57) ABSTRACT

The invention provides an assay for determining whether a test agent is a COX modulator. In general terms, the assay includes: determining whether a test agent modulates binding of a PDZ-containing polypeptide to a COX PL-containing polypeptide. The PDZ-containing polypeptide may contain the PDZ domain of PDZ domain of MAGI1, TIP-1, MAST2, PSD95, or SHANK. The assays may be done in a cell-free environment or in a cellular environment, particularly using a neuronal cell. The invention finds use in a variety of therapeutic applications, including for identifying agents for use in treating cancer, pain, inflammation and neuronal conditions caused by acute insult, e.g., stroke.

22 Claims, 18 Drawing Sheets

OTHER PUBLICATIONS

Sattler et al., "Specific coupling of NMDA receptor activation to nitric oxide neurotoxicity by PSD-95 protein," *Science, American Association for the Advancement of Science*, 284(5421):1845-1848 (1999).

Schwarze et al, "In vivo Protein Transduction: Delivery of Biologically active protein into the mouse", *Science*, 285:1569-1572, (1999).

Supplementary Partial European Search Report mailed Dec. 09, 2008 for Application 06785433.1.

Tang et al., "Flavonoids from Radix scutellariae as potential stroke therapeutic agents by targeting the second postsynaptic density 95 (PSD-95)/disc large/zonula occludens-1 (PDZ) domain of PSD-95", *Phytomedicine*, 11(4):277-284, (2004).

Weggen et al., "A subset of NSAIDs lower amyloidogenic A-beta-42 independently of cyclooxygenase activity", *Nature*, 414:212-216, (2001).

* cited by examiner

Shank-1 PDZ domain

*Minimal length*
VLLQKKDSEGFGFVLRGAKAQTPIEEFTPTPAFPALQYLESVDEGGVAWRAGLRMGDFLIEVNGQNVVKVGHRQVVNMIRQGGNTLM
VK        (SEQ. ID NO. 1)

*Intermediate length*
GSDYIIKEKTVLLQKKDSEGFGFVLRGAKAQTPIEEFTPTPAFPALQYLESVDEGGVAWRAGLRMGDFLIEVNGQNVVKVGHRQVVN
MIRQGGNTLMVKVVMVTRHPDM        (SEQ. ID NO. 2)

*+10 length*
apslmdgigpGSDYIIKEKTVLLQKKDSEGFGFVLRGAKAQTPIEEFTPTPAFPALQYLESVDEGGVAWRAGLRMGDFLIEVNGQNV
VKVGHRQVVNMIRQGGNTLMVKVVMVTRHPDMdeavhkkapq        (SEQ. ID NO. 3)

Shank-2 PDZ domain

*Minimal length*
VVLQKKDNEGFGFVLRGAKADTPIEEFTPTPAFPALQYLESVDEGGVAWQAGLRTGDFLIEVNNENVVKVGHRQVVNMIRQGGNHLV
LK        (SEQ. ID NO. 4)

*Intermediate length*
YSDCIIEEKTVVLQKKDNEGFGFVLRGAKADTPIEEFTPTPAFPALQYLESVDEGGVAWQAGLRTGDFLIEVNNENVVKVGHRQVVN
MIRQGGNHLVLKVVTVTRNLDP        (SEQ. ID NO. 5)

*+10 length*
nngrcprnslYSDCIIEEKTVVLQKKDNEGFGFVLRGAKADTPIEEFTPTPAFPALQYLESVDEGGVAWQAGLRTGDFLIEVNNENV
VKVGHRQVVNMIRQGGNHLVLKVVTVTRNLDPddtarkkapp        (SEQ. ID NO. 6)

Shank-3 PDZ domain

*Minimal length*
AVLQKRDHEGFGFVLRGAKAETPIEEFTPTPAFPALQYLESVDVEGVAWRAGLRTGDFLIEVNGVNVVKVGHKQVVALIRQGGNRLV
MK        (SEQ. ID NO. 7)

*Intermediate length*
HSDYVIDDKVAVLQKRDHEGFGFVLRGAKAETPIEEFTPTPAFPALQYLESVDVEGVAWRAGLRTGDFLIEVNGVNVVKVGHKQVVA
LIRQGGNRLVMKVVSVTRKPEE        (SEQ. ID NO. 8)

*+10 length*
tvgsydsltsHSDYVIDDKVAVLQKRDHEGFGFVLRGAKAETPIEEFTPTPAFPALQYLESVDVEGVAWRAGLRTGDFLIEVNGVNV
VKVGHKQVVALIRQGGNRLVMKVVSVTRKPEEdgarrramkk        (SEQ. ID NO. 9)

Mast-2 PDZ domain

*Minimal length*
IHRAGKKYGFTLRAIRVYMGDSDVYTVHHMVWHVEDGGPASEAGLRQGDLITHVNGEPVHGLVHTEVVELILKSGNKVA        (SEQ.
ID NO. 10)

*Intermediate length*
ALGSMRPPIIIHRAGKKYGFTLRAIRVYMGDSDVYTVHHMVWHVEDGGPASEAGLRQGDLITHVNGEPVHGLVHTEVVELILKSGNK
VAISTTPLENTS        (SEQ. ID NO. 11)

*+10 length*
dsspsrdflpALGSMRPPIIIHRAGKKYGFTLRAIRVYMGDSDVYTVHHMVWHVEDGGPASEAGLRQGDLITHVNGEPVHGLVHTEV
VELILKSGNKVAISTTPLENTSikvgparkgs        (SEQ. ID NO. 12)

COX-2 PDZ ligand

LLKERSTEL        (SEQ. ID NO. 13)

The terminal (position 0) Leu may be substituted by Ile, Val, Phe, Tyr, Met or Ala.
The Glu at position -1 may be substituted by Glu, Asp, Gln, Asn, Arg, Lys, Val, Leu or
Met.
The Thr at position -2 may be substituted by Ser, Tyr or Val.

*FIG. 1A*

CLUSTAL X (1.81) multiple sequence alignment

```
Other Mutations          S----RDRS--II-R-ET--L---K----N---DD-------E--------------K
hShank1_PDZminimal       GSDYIIKEKTVLLQKKDSEGFGFVLRGAKAQTPIEEFTPTPAFPALQYLESVDEGGVAWR
hShank2_PDZminimal       YSDCIIEEKTVVLQKKDNEGFGFVLRGAKADTPIEEFTPTPAFPALQYLESVDEGGVAWQ
hShank3_PDZminimal       HSDYVIDDKVAVLQKRDHEGFGFVLRGAKAETPIEEFTPTPAFPALQYLESVDVEGVAWR
hMAST2_PDZminimal        ---ALGSMRPPIIHRAGKKYGFTLRAIRVY----
hMAST2_PDZminimal        MGDSDVYTVHHMVWHVEDGGPASE
                         :.: .**  **  . :::: ** .**.  *: .*

Other Mutations          ----E-VL-------R-----------RLL--K--
hShank1_PDZminimal       AGLRMGDFLIEVNGQNVVKVGHRQVVNMIRQGGNTLMVKVVMVTRHPDM
hShank2_PDZminimal       AGLRTGDFLIEVNNENVVKVGHRQVVNMIRQGGNHLVLKVTVTRNLDP
hShank3_PDZminimal       AGLRTGDFLIEVNGVNVVKVGHKQVVALIRQGGNRLVMKVVSVTRKPEE
hMAST2_PDZminimal        AGLRQGDLITHVNGEPVHGLVHTEVVELILKSGNKVAISTTPLENTS---
                         ****:**:: *   .* :. : :***::: .**.: :: .* * : .
```

Description of above protein sequence alignment
Shank1, Shank2, Shank3, hMAST2 all bind COX-2 PDZ ligand. Therefore, single substitutions down each column are tolerated across the four PDZs listed in terms of allowing for COX-2 binding to the PDZ. Additional conservative mutations are also written in the row "Other Mutations".

FIG. 1B

```
Shank1    GSDYIIKEKTVLLQKKDSEGFGFVLRGAKAQTPIEEFTPTPAFPALQYLESVDEGGVAWR  60
Shank2    YSDCIIEEKTVVLQKKDNEGFGFVLRGAKADTPIEEFTPTPAFPALQYLESVDEGGVAWQ  60
Shank3    ISDYVIDDKVAVLQKRDHEGFGFVLRGAKAETPIEEFTPTPAFPALQYLESVDVEGVAWR  60
          .*  :*..:.*::**:.*:*************:*********************:*.****:

Shank1    AGLRMGDFLIEVNGQNVVKVGHRQVVNMIRQGGNTLMVKVVMVTRHPDM  109 (SEQ. ID NO. 2)
Shank2    AGLRTGDFLIEVNNENVVKVGHRQVVNMIRQGGNHLVLKVVTVTRNLDP  109 (SEQ. ID NO. 5)
Shank3    AGLRTGDFLIEVNGVNVVKVGHKQVVALIRQGGNRLVMKVVSVTRKPEE  109 (SEQ. ID NO. 8)
          ****:********. ******:***:*******:*::***:.***: ::
```

FIG. 2

Peptide 1956 COX2-TAT
Concentration of 0.06uM
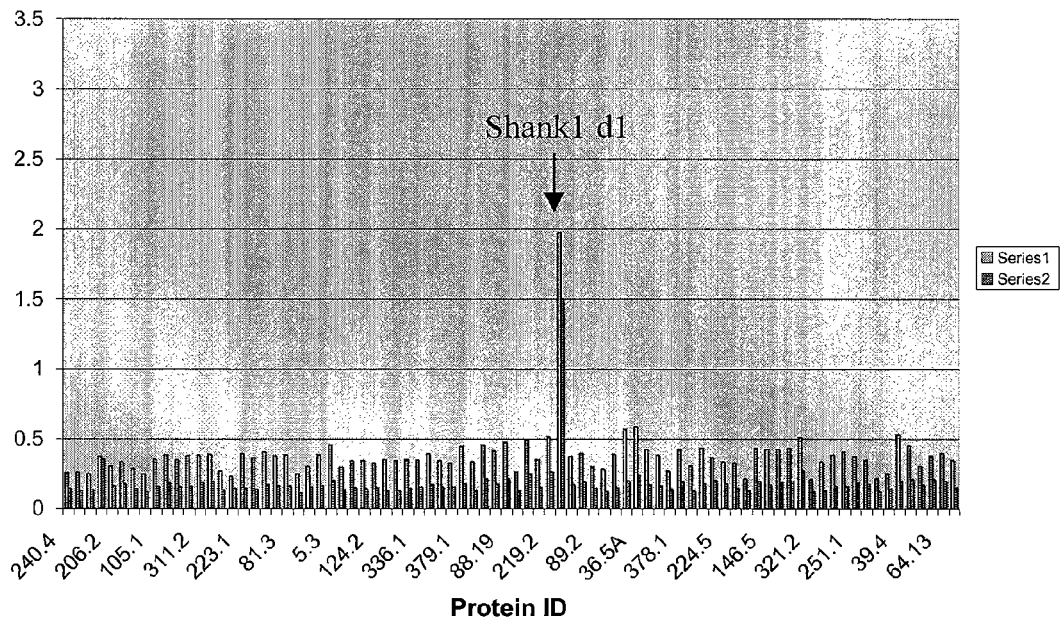
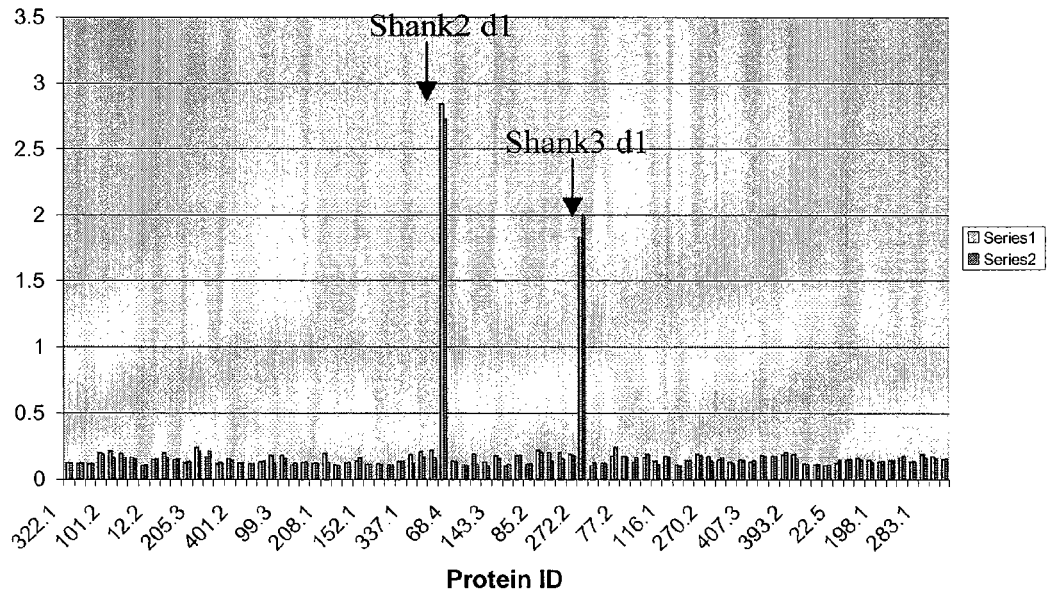
*FIG. 3A*

Peptide 1956 COX2-TAT Concentration of 0.06uM
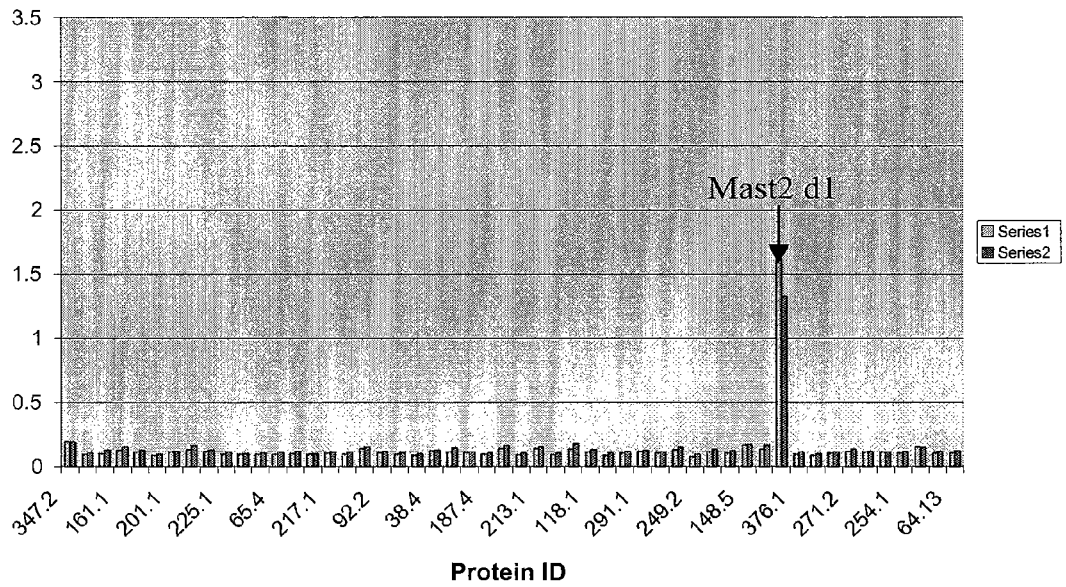
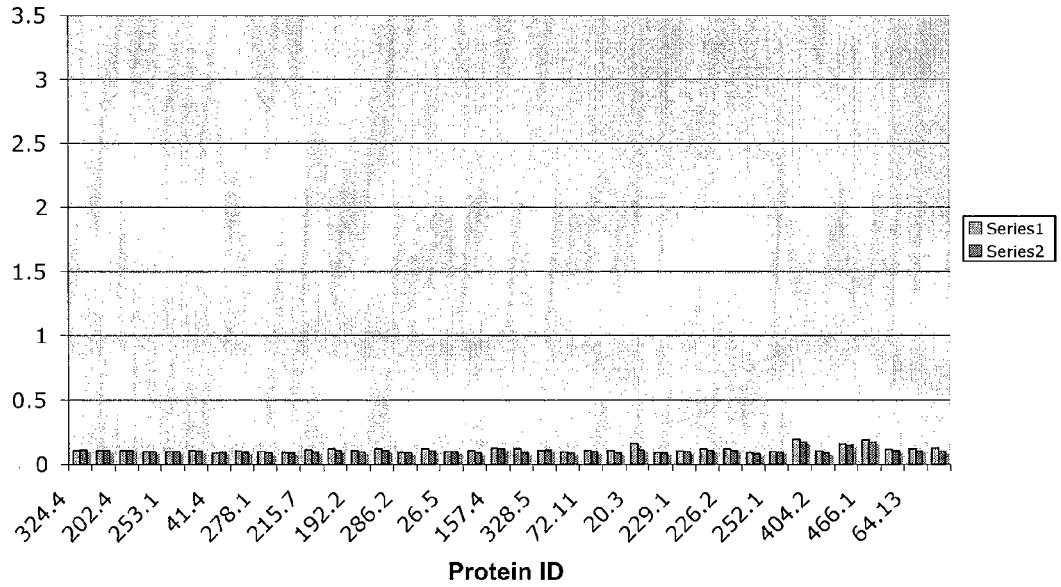
*FIG. 3B*

FIGURE 5A

| | | |
|---|---|---|
| KIAA 1481 | PIPAGGCTFSGIFPTLTSPL | SEQ ID NO: 26 |
| VIPS_human | LQFHRGSRAQSFLQTETSVI | SEQ ID NO: 27 |
| DNAM-1 | TREDIYVNYPTFSRRPKTRV | SEQ ID NO: 28 |
| PAG | KENDYESISDLQQGRDITRL | SEQ ID NO: 29 |
| LPAP | AWDDSARAAGGQGLHVTAL | SEQ ID NO: 30 |
| CDw128B | KDSRPSFVGSSSGHTSTTL | SEQ ID NO: 31 |
| CFTCR (cystic fibrosis transmembrane conductance regulator) | KPQIAALKEETEEEVQDTRL | SEQ ID NO: 32 |
| BLR-1 | PSWRRSSLSESENATSLTTF | SEQ ID NO: 33 |
| HPV E6 33 (modified) | AAGGRSARGGRLQGRRETAL | SEQ ID NO: 34 |
| Na+/Pi cotransporter 2 | PPATPSPRLALPAHHNATRL | SEQ ID NO: 35 |
| Neuroligin | TFAAGFNSTGLPHSTTRV | SEQ ID NO: 36 |
| PTEN | DSDPENEPFDEDQHTQITKV | SEQ ID NO: 37 |
| alpha-2B Adrenergic receptor | QDFRRAFRRILARPWTQTAW | SEQ ID NO: 38 |
| Fas Ligand | SSKSKSSEESQTFFGLYKL | SEQ ID NO: 39 |
| somatostatin receptor 4 | EALQPEPGRKRIPLTRTTTF | SEQ ID NO: 40 |
| DOCK2 | LASKSAEEGKQIPDSLSTDL | SEQ ID NO: 41 |
| Tat-TIAM 1 | YGRKKRRQRRRPSRKLNTEI | SEQ ID NO: 42 |
| PAR-2 | KHSRKSSSYSSSSTTVKTSY | SEQ ID NO: 43 |
| PTEN | DSDPENEPFDEDQHTQITKV | SEQ ID NO: 44 |
| Guanylate kinase-associated protein | SATESAESIEIYIPEAQTRL | SEQ ID NO: 45 |

FIGURE 5B

| | | |
|---|---|---|
| TRAF2 | NSYVRDDAIFIKAIVDLTGL | SEQ ID NO: 46 |
| LPAP | AWDDSARAAGGQGLHVTAL | SEQ ID NO: 47 |
| Dopamine transporter | RELVDRGEVRQFTLRHWLKV | SEQ ID NO: 48 |
| GluR delta-2 | QPTPTLGLNLGNDPDRGTSI | SEQ ID NO: 49 |
| PTEN | DSDPENEPFDEDQHTQITKV | SEQ ID NO: 50 |
| CD46 | KKGTYLTDETHREVKFTSL | SEQ ID NO: 51 |
| alpha-2B Adrenergic receptor | QDFRRAFRRILARPWTQTAW | SEQ ID NO: 52 |
| AdenoE4 typ9 | VGTLLLERVIFPSVKIATLV | SEQ ID NO: 53 |
| CDw128B | KDSRPSFVGSSSGHTSTTL | SEQ ID NO: 54 |
| Neuroligin | TFAAGFNSTGLPHSTTRV | SEQ ID NO: 55 |
| DNAM-1 | TREDIYVNYPTFSRRPKTRV | SEQ ID NO: 56 |
| BLR-1 | PSWRRSSLSESENATSLTTF | SEQ ID NO: 57 |
| DOCK2 | LASKSAEEGKQIPDSLSTDL | SEQ ID NO: 58 |
| KIAA 1481 | PIPAGGCTFSGIFPTLTSPL | SEQ ID NO: 59 |
| presenilin-1 | ATDYLVQPFMDQLAFHQFYI | SEQ ID NO: 60 |
| HPV E6 #66 (cysteine-free) | TGSALQAWRHTSRQATESTV | SEQ ID NO: 61 |
| PAG | KENDYESISDLQQGRDITRL | SEQ ID NO: 62 |
| Fas Ligand | SSKSKSSEESQTFFGLYKL | SEQ ID NO: 63 |
| HPV E6 58 (modified) | AVGGRPARGGRLQGRRQTQV | SEQ ID NO: 64 |
| HPV E6 33 (modified) | AAGGRSARGGRLQGRRETAL | SEQ ID NO: 65 |
| a-actinin 2 | VPGALDYAAFSSALYGESDL | SEQ ID NO: 66 |
| NMDA Glutamate Receptor 2C (cysteine-free) | TQGFPGPATWRRISSLESEV | SEQ ID NO: 67 |
| Na+/Pi cotransporter 2 | PPATPSPRLALPAHHNATRL | SEQ ID NO: 68 |
| HPV E6 #35 (cysteine-free) | GRWTGRAMSAWKPTRRETEV | SEQ ID NO: 69 |
| CITRON protein | AGAVRTPLSQVNKVWDQSSV | SEQ ID NO: 70 |
| catenin - delta 2 | PYSELNYETSHYPASPDSWV | SEQ ID NO: 71 |
| KIAA 1481 | PIPAGGCTFSGIFPTLTSPL | SEQ ID NO: 72 |
| zona occludens 3 (ZO-3) | VHDAESSDEDGYDWGPATDL | SEQ ID NO: 73 |
| NMDA | LNSCSNRRVYKKMPSIESDV | SEQ ID NO: 74 |
| CD34 | QATSRNGHSARQHVVADTEL | SEQ ID NO: 75 |
| MINT-1 | KTMPAAMYRLLTAQEQPVYI | SEQ ID NO: 76 |
| serotonin receptor 5HT-2B | DTLLLTENEGDKTEEQVSYV | SEQ ID NO: 77 |
| noradrenaline transporter | HHLVAQRDIRQFQLQHWLAI | SEQ ID NO: 78 |
| Mannose Receptor | GTSDMKDLVGNIEQNEHSVI | SEQ ID NO: 79 |
| TATNMDA2B9 | YGRKKRRQRRRKLSSIESDV | SEQ ID NO: 80 |
| VIPS human | LQFHRGSRAQSFLQTETSVI | SEQ ID NO: 81 |
| TAX | QISPGGLEPPSEKHFRETEV | SEQ ID NO: 82 |
| Tat-TIAM 1 | YGRKKRRQRRRPSRKLNTEI | SEQ ID NO: 83 |
| KV1.3 | TTNNNPNSAVNIKKIFTDV | SEQ ID NO: 84 |
| CFTCR (cystic fibrosis transmembrane conductance regulator) | KPQIAALKEETEEEVQDTRL | SEQ ID NO: 85 |

PSD95 Accession AAC52113

PSD95 d1 PDZ
LEYEEITLERGNSGLGFSIAGGTDNPHIGDDPSIFITKIIPGGAAAQDGRLRVNDSILFVNE
VDVREVTHSAAVEALKEAGSIVRLYVMRRKPPAE (SEQ. ID NO. 86)

PSD95 d2 PDZ
GIHVMRRKPPAEKVMEIKLIKGPKGLGFSIAGGVGNQHIPGDNSIYVTKIIEGGAAHKDG
RLQIGDKILAVNSVGLEDVMHEDAVAALKNTYDVVYLKVAKPSNAYL (SEQ. ID NO. 87)

PSD95 d3 PDZ
PVAKDLLGEEDIPREPRRIVIHRGSTGLGFNIVGGEDGEGIFISFILAG
GPADLSGELRKGDQILSVNGVDLRNASHEQAAIALKNAGQTVTIIAQYKP
EEYSRFEAKIHDLREQLMNSS (SEQ. ID NO.88)

Magi1 d1 Accession Q96QZ7
Magi1 d1 PDZ
PSELKGKFIHTKLRKSSRGFGFTVVGGDEPDEFLQIKSLVLDGPAALDGKMETGDVIVSV
NDTCVLGHTHAQVVKIFQSIPIGASVDLELCRGYPLPFDPD (SEQ. ID NO. 89)

TIP1 Accession AF028823
TIP1 PDZ sequence
QRVEIHKLRQGENLILGFSIGGGIDQDPSQNPFSEDKTDKGIYVTRVSEGGPAEIAGLQIG
DKIMQVNGWDMTMVTHDQARKRLTKRSEEVVRLLVTRQSLQK
(SEQ. ID NO. 90)

FIG. 6

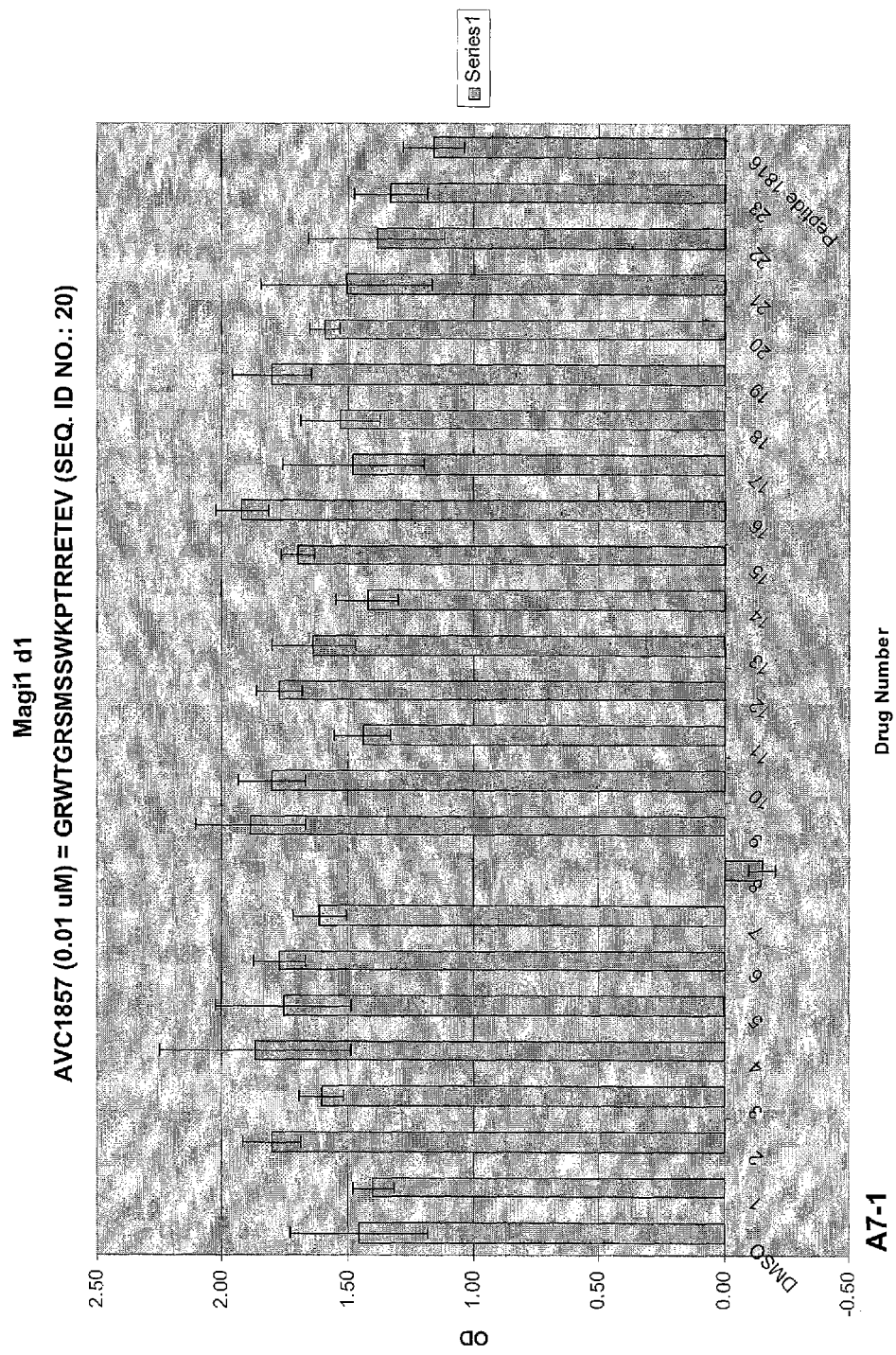
*FIG. 7A*: MAGI1 d1/AVC1857

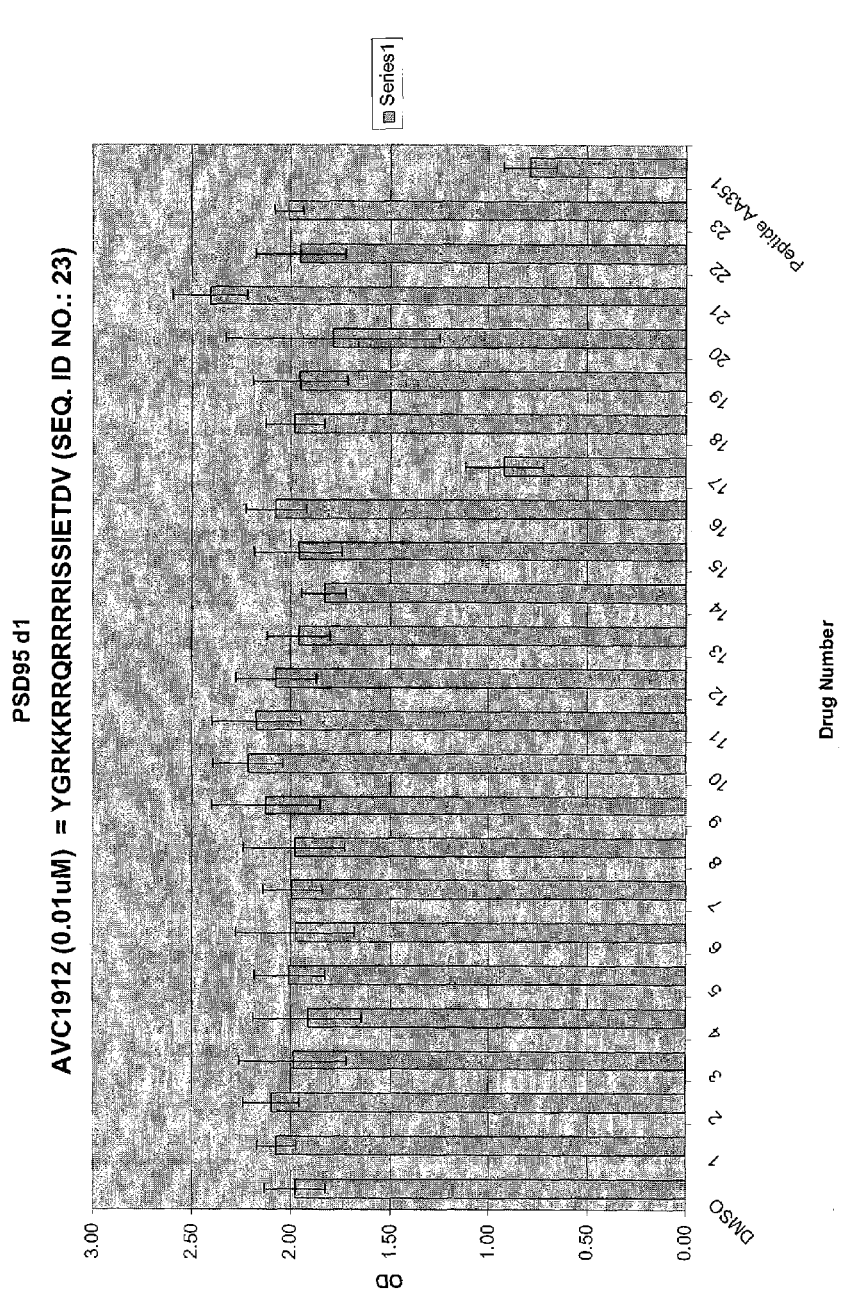
FIG. 7B: PSD95 d1/AVC1912

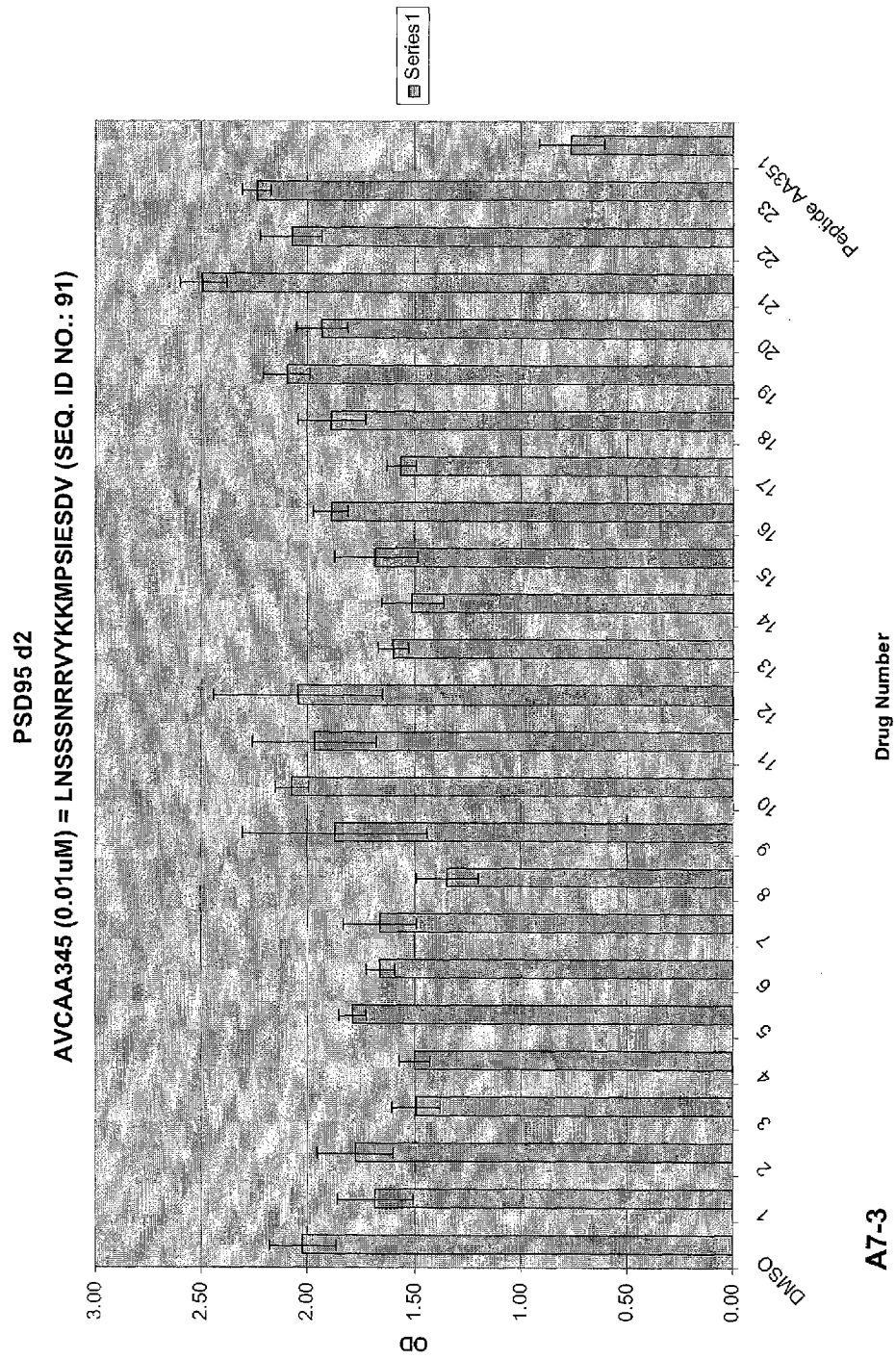
FIG. 7C: PSD95 d2/AVCAA345

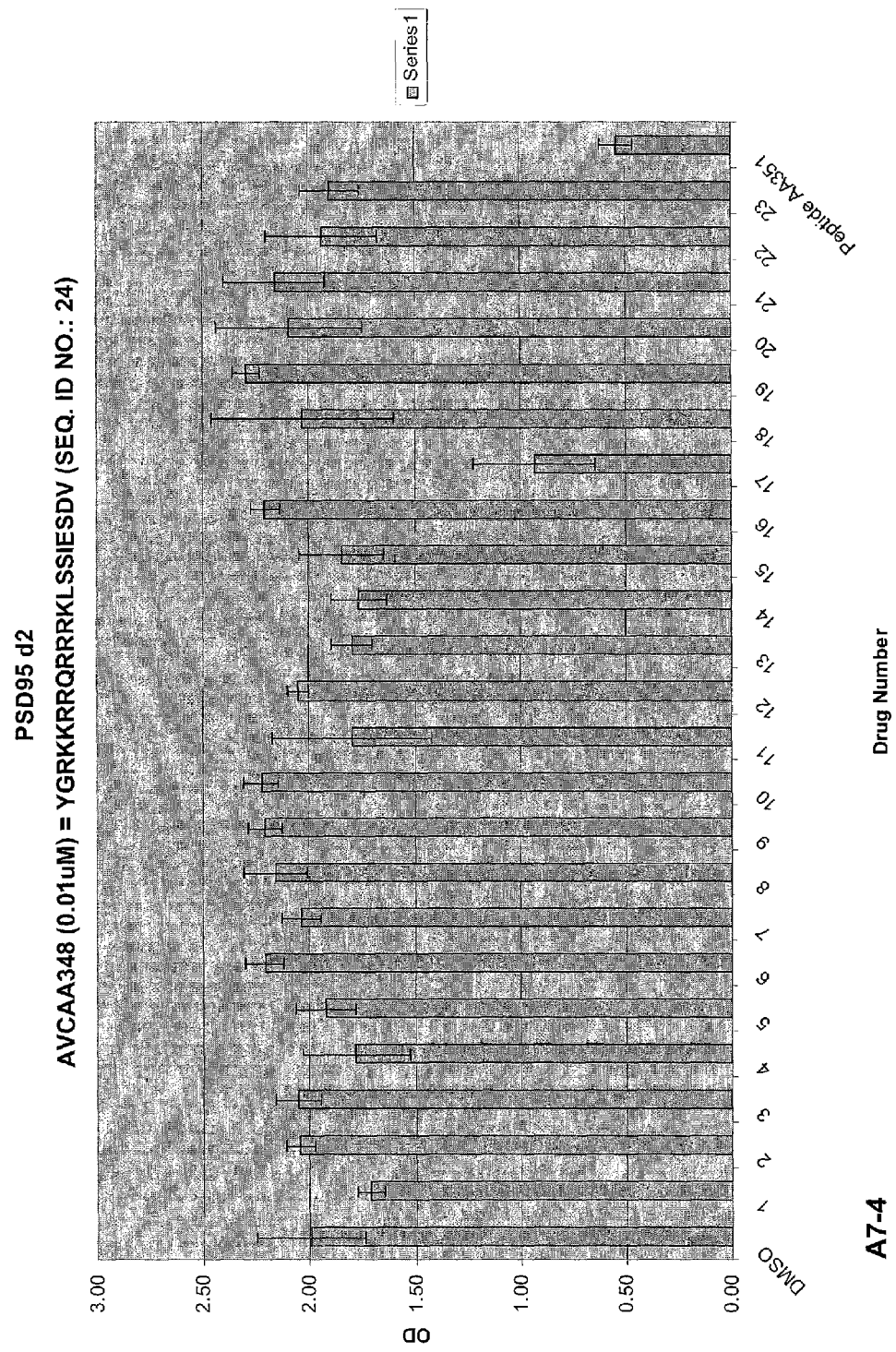
FIG. 7D: PSD95 d2/AVCAA348

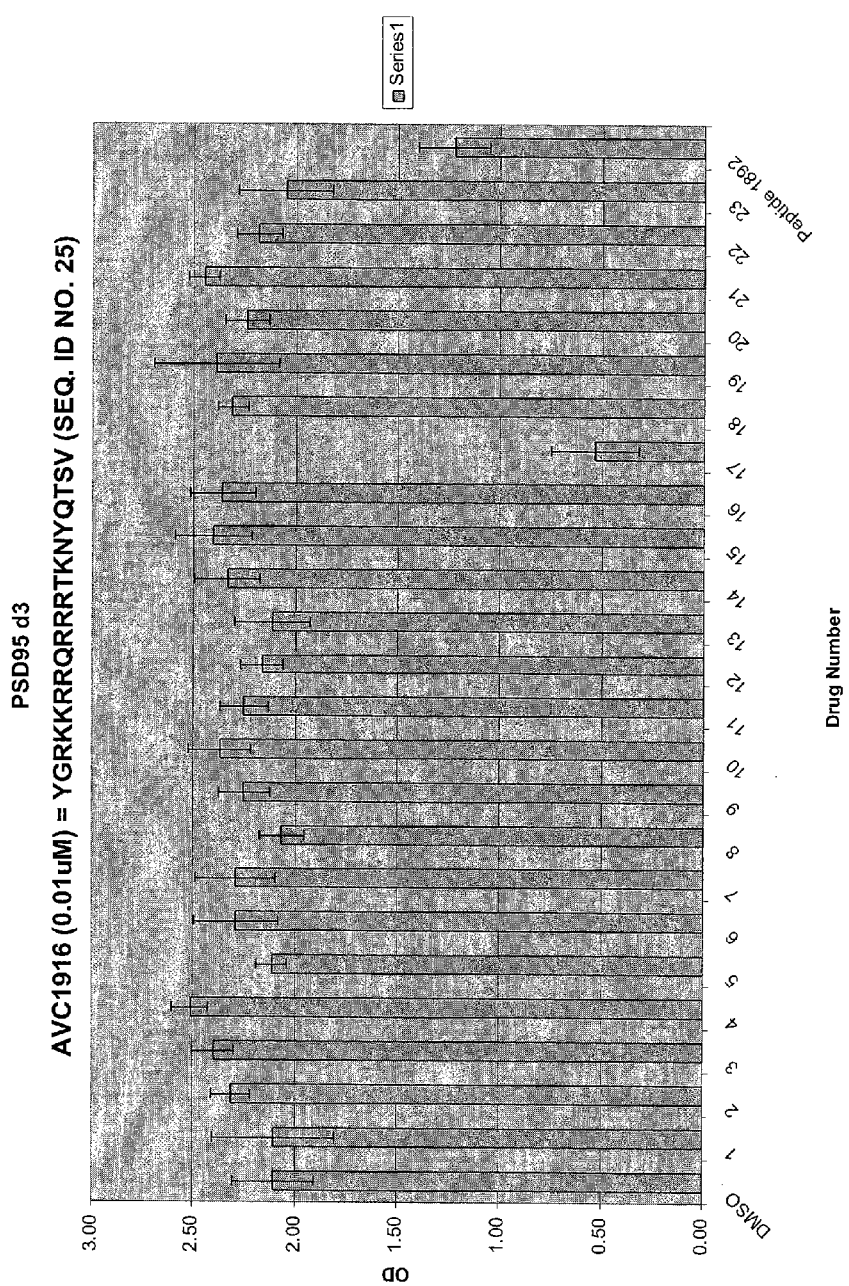
FIG. 7E: PSD95 d3/AVC1916

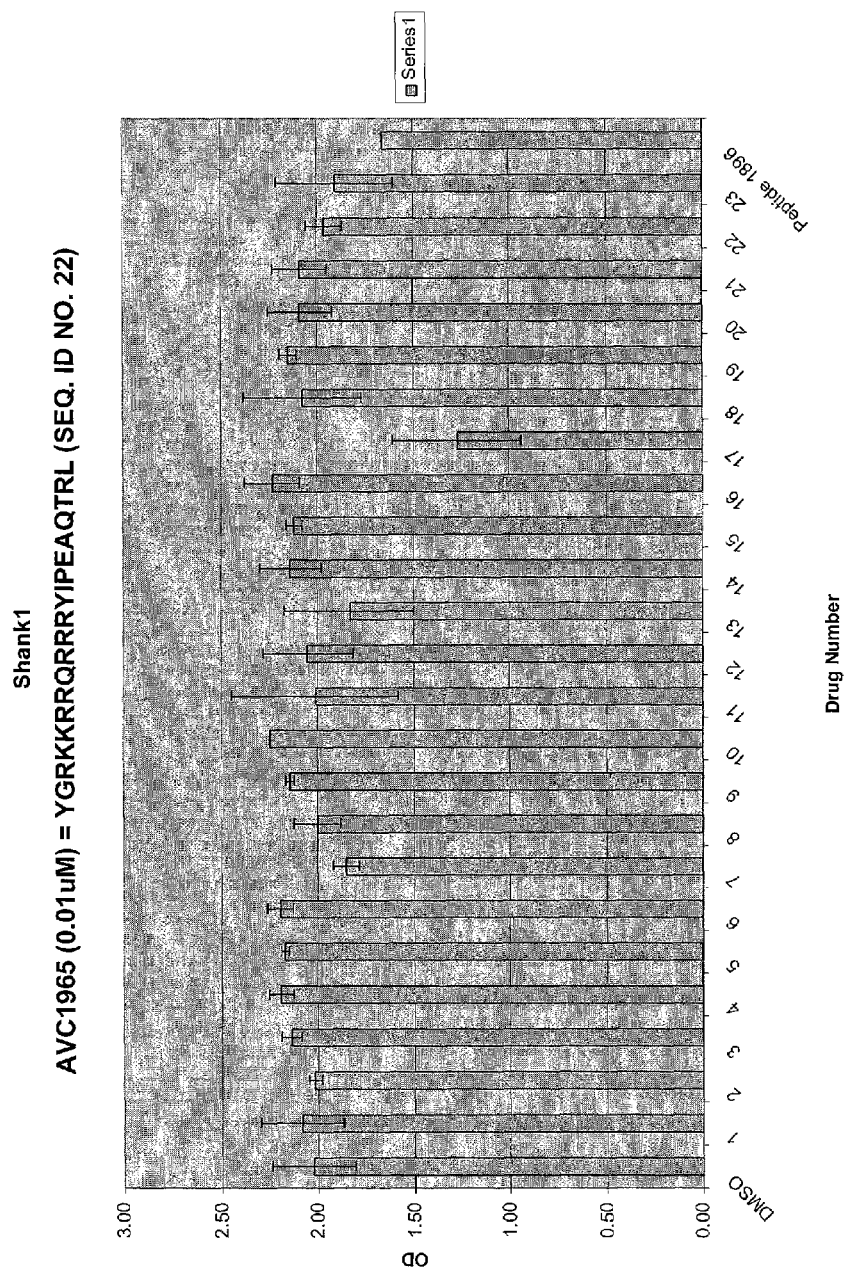
FIG. 7F: Shank1/AVC1965

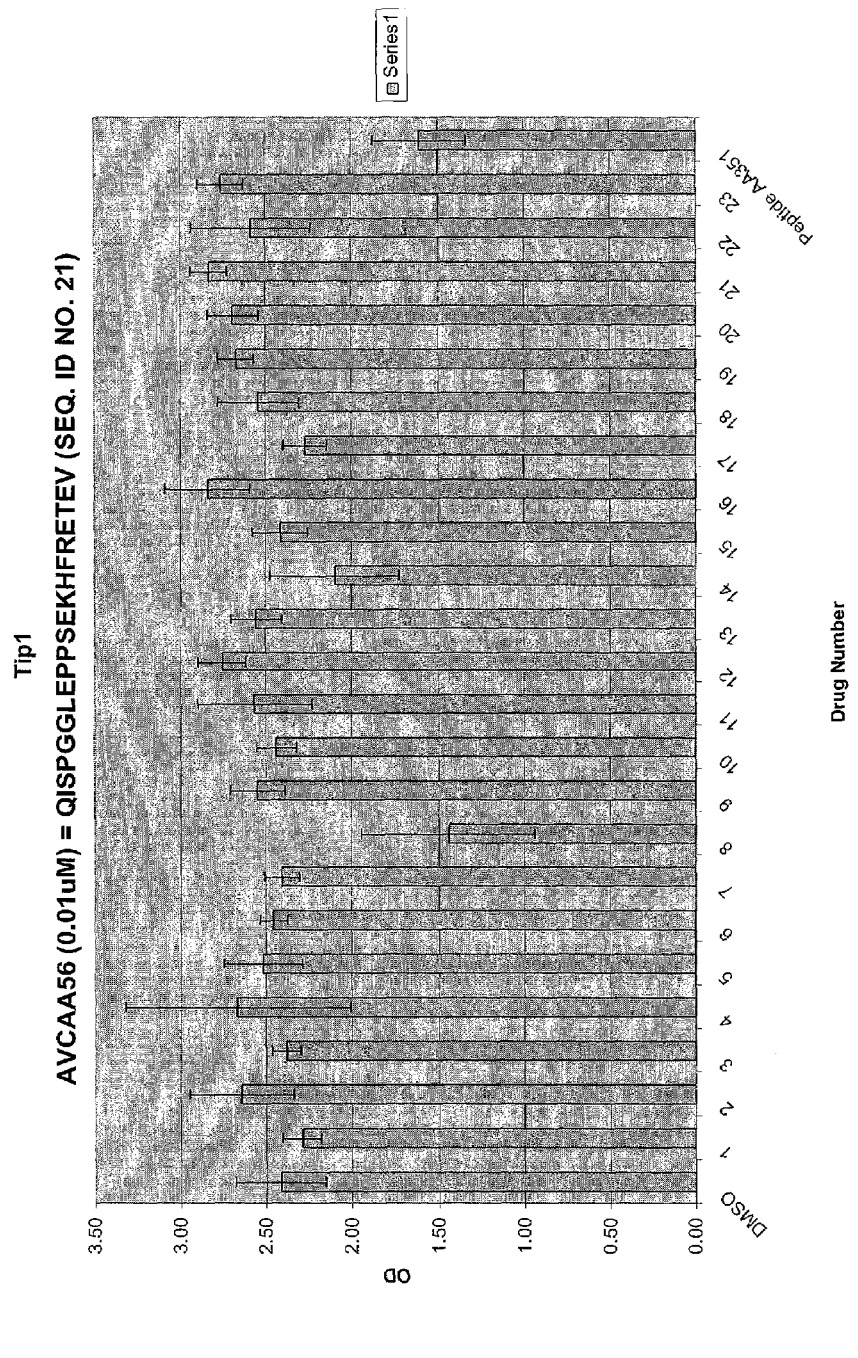
FIG. 7G: TIP1/AVCAA56

ASSAYS FOR DETECTING INHIBITORS OF BINDING BETWEEN COX-2 AND PDZ PROTEINS

CROSS-REFERENCES TO RELATED APPLICATIONS

This application claims the benefit of the priority date under 35 U.S.C. § 119(e) of U.S. Provisional Application No. 60/693,988, filed Jun. 23, 2005, the contents of which are herein incorporated by reference in their entirety.

BACKGROUND OF THE INVENTION

The prostaglandins are a potent class of biologically active lipid derivatives that play a crucial role in the inflammatory response. The inflammatory response is a localized tissue response to injury or other trauma characterized by pain, heat, redness and swelling. Prostaglandins mediate this response by inhibiting platelet aggregation, increasing vascular permeability, increasing vascular dilation, inducing smooth-muscle contraction and causing the induction of neutrophil chemotaxis. Because of their central role in mediating the inflammatory response, significant efforts have been directed toward elucidating compositions that are capable of inhibiting the biosynthesis of prostaglandins.

Toward that end, prostaglandin biosynthesis has been extensively characterized. Prostaglandins are a group of oxygenated fatty acids that are generally derived from arachidonic acid. The biosynthesis of prostaglandins from arachidonic acid occurs in a three step process that includes 1) hydrolysis of arachidonic acid from phospholipid precursors catalyzed by a phospholipase $A_2$; 2) cyclooxygenase ("COX") catalyzed oxygenation of arachidonic acid to prostaglandin G2 ("PGG2"). This COX catalyzed reaction is the first committed and rate limiting step in prostaglandin synthesis; and 3) conversion of prostaglandin G2 to the biologically active end product, prostaglandin, catalyzed by a series of synthases and reductases. Upon their synthesis, prostaglandins exit the cell and act in a hormone-like manner by affecting the target cell via G protein linked membrane receptors.

Inactivation of the COX enzyme is a natural target as a means to inhibit prostaglandin production due to this enzyme's pivotal role in the prostaglandin biosynthetic pathway. It is now known that two gene products possessing COX enzyme activity are expressed, termed COX-1 and COX-2. COX-1 was the first discovered isoform and is constitutively expressed in most tissue types. Because it is constitutively expressed, COX-1 is available to participate in activities requiring a rapid physiological response and causes the production of prostaglandins involved in "house-keeping" functions. For example, COX-1 is responsible for acute production of prostaglandins that regulate vascular homeostasis, maintain gastrointestinal integrity, and maintain kidney function. Thus, COX-1 activity is responsible for the synthesis of prostaglandins required for the maintenance of several cell types.

COX-2, on the other hand, is a recently discovered isoform that is inducibly expressed in response to numerous stimuli such as bacterial lipopolysaccharides, growth factors, cytokines, and phorbol esters. In addition, COX-2 is only expressed in a limited number of cell types including monocytes, macrophages, neutrophils, fibroblasts and endothelial cells. COX-2 expression, but not COX-1 expression, has been shown to increase in rheumatoid synovial tissue. Contrastingly, COX-2 expression is inhibited in response to glucocorticoids and by anti-inflammatory cytokines. Thus, based upon these observations, COX-2 has been shown to be the isoform responsible for mediating the production of prostaglandins that participate in the inflammatory response and inflammatory related disorders. In addition, COX-2 has also been shown to participate in certain cancers, Alzheimer's disease, atherosclerosis, and central nervous system damage resulting from stroke, ischemia and trauma.

Nonsteroidal anti-inflammatory drugs (NSAIDs) are also utilized as a means to reduce effects associated with the inflammatory response. The principal pharmaceutical effects of NSAIDs are due to their ability to prevent COX activity resulting in the inhibition of prostaglandin synthesis. Inhibition of prostaglandin synthesis by NSAIDs is anti-pyretic, analgesic, anti-inflammatory, and anti-thrombogenic. However, administration of NSAIDs may also result in severe side effects such as gastrointestinal bleeding, ulcers and incidence of renal problems.

There is a great need for new drugs that modulate COX activity, as well as assays to facilitate the discovery of such drugs. This invention meets this need.

BRIEF SUMMARY OF THE INVENTION

In certain aspects, the invention provides an assay for determining whether a test agent is a COX modulator. In general terms, the assay includes: determining whether a test agent modulates binding of a PDZ-containing polypeptide to a COX PL-containing polypeptide. The PDZ-containing polypeptide may contain the PDZ domain of PDZ domain of MAGI1, TIP-1, MAST2, PSD95, or SHANK. The assays may be done in a cell-free environment or in a cellular environment, particularly using a neuronal cell. The invention finds use in a variety of therapeutic applications, including for identifying agents for use in treating pain, cancer, inflammation and neuronal conditions caused by acute insult, e.g., stroke.

The invention is based on the discovery that COX-2 contains a PDZ ligand (i.e., an amino acid sequence that binds to PDZ proteins; or "PL" for short) at its C-terminus, and the further discovery of the cellular PDZ-containing proteins to which COX-2's PDZ ligand binds.

In another aspect of the invention, it has also been found that COX-1 contains a PDZ ligand (i.e., and amino sequence that binds to PDZ proteins; or "PL" for short) at its C-terminus.

The discovery of the cellular proteins to which COX-2 binds allows assays to be performed in order to identify COX-2 modulatory agents. The COX-2 modulatory agents may, in certain embodiments, inhibit binding between COX-2 and the subject PDZ-domain containing binding proteins. In other embodiments, inhibitors of cycloxygenase activity of COX-2 may be tested in the subject binding assays to identify inhibitors that do or do not modulate binding of COX-2 to the subject PDZ domain-containing proteins.

In certain aspects, COX-2 binds to all three members of the SHANK family (which includes SHANK1, SHANK2 and SHANK3). Proteins of the SHANK family are known to interact with components of the postsynaptic membrane, including NMDA receptors, metabotropic glutamate receptors and the actin-based cytoskeleton. For example, SHANK1 is known to be expressed in neuronal tissues and modulates synaptic responses by interaction with inhibitory G-proteins in pre- and post-synaptic compartments. Further, SHANK1 is known to act as scaffold in the post-synaptic density (PSD), crosslinking NMDA receptor/PSD95 complexes and coupling them to cytoskeleton regulators. SHANK1 also crosslink Homer/PSD95 complexes, and mediates mGluR and NMDA receptor signaling. SHANK2 is expressed only in the brain, and SHANK3 is expressed mainly in the cerebral cortex and is highly enriched in the PSD/excitatory synapses.

Accordingly, in accordance with certain aspects of the invention, COX-2, as well as having a cycloxygenase activity that is involved in the production of prostaglandins, may have a binding activity that is involved in NMDA receptor activation in brain tissue. Inhibitors of binding between COX-2 and PDZ-containing proteins, in certain embodiments, may be employed to treat acute insults to nerve tissue, such as ischemic events (including stroke or cardiac arrest), hypoxic events and trauma, as well as other neuron-related conditions and cancers.

BRIEF DESCRIPTION OF THE DRAWINGS

FIG. 1A shows SHANK1, SHANK2, SHANK3 and MAST2 PDZ domain and COX-2 PDZ ligand sequence that may be employed herein. Minimally-lengthed PDZ domains are shown, as well as exemplary PDZ domains of longer length.

FIG. 1B shows a sequence alignment of SHANK1 (SEQ ID NO: 2), SHANK2 (SEQ ID NO: 5), SHANK3 (SEQ ID NO: 8) and MAST2 (SEQ ID NO: 11) PDZ domains indicating amino acids that substitutions may be made.

FIG. 2 shows an amino acid sequence alignment between the PDZ domains of the SHANK1, SHANK2 and SHANK3.

FIG. 3A-3B shows exemplary results identifying SHANK1, SHANK2, SHANK3 and MAST2 as COX-2 binding proteins.

FIGS. 5A and 5B shows the sequences of polypeptides that can bind to the PDZ domain at least one SHANK polypeptide (FIG. 5A) and the PDZ domain of MAST2 (FIG. 5B).

FIG. 6 shows amino acid sequences for MAGI1 d1, TIP-1, PSD95 d1, PSD95 d2, and PSD95 d3 PDZ domain sequences that may be employed in accordance with certain embodiments of the present invention.

FIGS. 7A-7G show exemplary results from assays screening exemplary candidate small molecule drug therapeutics in accordance with various embodiments of the invention.

DETAILED DESCRIPTION OF THE INVENTION

I. Definitions

Figure 4A:
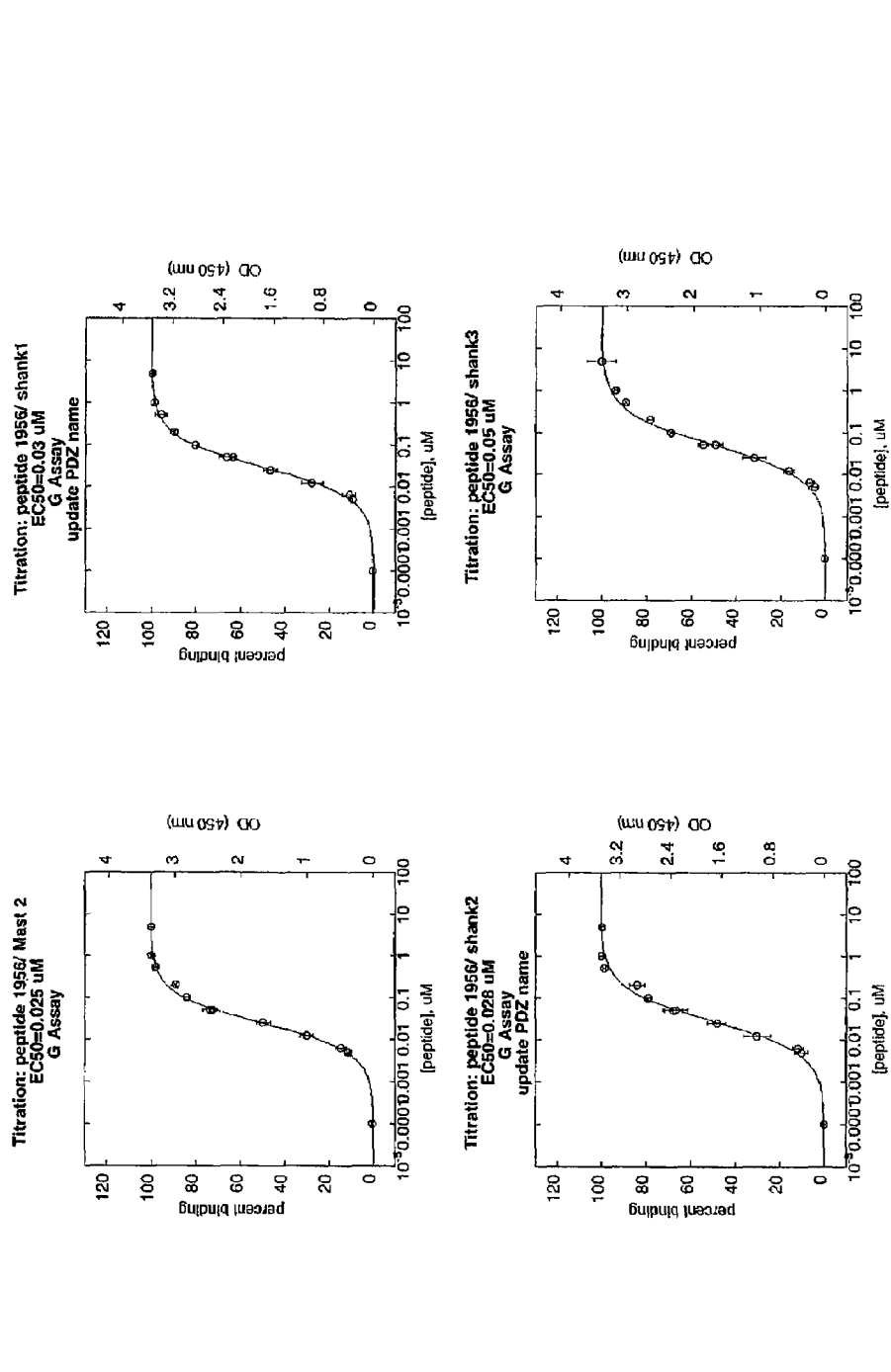
FIG. 4A-4C shows further exemplary results identifying SHANK1, SHANK2, SHANK3 and MAST2 as COX-2 binding proteins (SEQ ID NO: 15).

Unless defined otherwise, all technical and scientific terms used herein have the same meaning as commonly understood by those of ordinary skill in the art to which this invention pertains. The following references provide one of skill with a general definition of many of the terms used in this invention: Singleton et al., *Dictionary of Microbiology and Molecular Biology* (2d Ed. 1994); *The Cambridge Dictionary of Science and Technology* (Walker Ed., 1988); and Hale & Marham, *The Harper Collins Dictionary of Biology* (1991). Although any methods and materials similar or equivalent to those described herein can be used in the practice or testing of the present invention, the preferred methods and materials are described. The following definitions are provided to assist the reader in the practice of the invention.

The term "modulation" as used herein refers to both upregulation, (i.e., activation or stimulation) for example by agonizing, and downregulation (i.e., inhibition or suppression) for example by antagonizing, of a bioactivity (e.g., a binding activity). As used herein, the term "COX PDZ ligand binding modulator" refers to an agent that is able to alter binding of the PDZ-ligand (i.e., "PL") of COX (e.g., COX-1 or COX-2 or both) with the PDZ domain of, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2. Modulators include, but are not limited to, both activators and inhibitors. An inhibitor may cause partial or complete inhibition of binding.

A "COX PDZ ligand binding modulator" generally reduces binding between COX-2 and a PDZ polypeptide by at least 20%, e.g., at least 30%, at least 40%, at least 50%, at least 60%, at least 70%, at least 80%, at least 90%, at least 95%, up to about 99% or 100%, as compared to controls that do not include the test compound. In general, agents of interest are those which exhibit $IC_{50}$s in a particular assay in the range of about 1 mM or less. Compounds which exhibit lower $IC_{50}$s, for example, in the range of about 100 µM, 10 µM, 1 µM, 100 nM, 10 nM, 1 nM, or even lower, are particularly useful for as therapeutics or prophylactics to treat or prevent COX-mediated disorders. Equivalent definitions will apply for COX-2 PDZ ligand binding modulators and COX-1 PDZ ligand binding modulators.

By "COX-inhibitory," "COX-1 inhibitory," or "COX-2-inhibitory", as in the context of a "COX-2-inhibitory compound", is meant having an activity that inhibits any activity of COX, COX-2, or COX-2, respectively, including, e.g., a cycloxygenase (i.e., the prostaglandin-producing) activity of COX-2, a binding activity of COX-2, or an ability of COX-2 to increase or decrease activation of the NMDA receptor.

A "COX-mediated disorder," "COX-1 mediated disorder," or "COX-2 mediated disorder" is any disorder that may be mediated by an activity of COX, COX-2, or COX-2, respectively. For example, many COX-2-mediated disorders involve inflammation and pain. COX-2-mediated disorders also include certain types of cancer, Alzheimer's disease, atherosclerosis, and central nervous system damage resulting from stroke, ischemia or trauma, for example.

As used herein, the term "acute insult to the central nervous system" includes short-term events that pose a substantial threat of neuronal damage mediated by glutamate excitotoxicity. These include ischemic events (which involve inadequate blood flow, such as a stroke or cardiac arrest), hypoxic events (involving inadequate oxygen supply, such as drowning, suffocation, or carbon monoxide poisoning), trauma to the brain or spinal cord (in the form of mechanical or similar injury), certain types of food poisoning which involve an excitotoxic poison such as domoic acid, and seizure-mediated neuronal degeneration, which includes certain types of severe epileptic seizures. It can also include trauma that occurs to another part of the body, if that trauma leads to sufficient blood loss to jeopardize blood flow to the brain (for example, as might occur following a shooting, stabbing, or automobile accident).

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably. Further, a "test agent" or "candidate agent" is generally a subject agent for use in an assay of the invention for investigation as a potential COX-2 PDZ ligand binding modulator.

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher binding affinity, or higher selectivity of binding to a target and lower activity levels to non-target molecules) is an approach that is well known in pharmaceutical chemistry.

As used herein, "contacting: has its normal meaning and refers to combining two or more agents (e.g., two proteins, a polynucleotide and a cell, etc.). Contacting can occur in vitro (e.g., two or more agents, such as a test compound and a cell lysate, are combined in a test tube or other container) or in situ (e.g., two polypeptides can be contacted in a cell by coexpression in the cell, of recombinant polynucleotides encoding the two polypeptides), in the presence or absence of a cell lysate.

A "biopolymer" is a polymer of one or more types of repeating units, regardless of the source. Biopolymers may be found in biological systems and particularly include polypeptides and polynucleotides, as well as such compounds containing amino acids, nucleotides, or analogs thereof. The term "polynucleotide" refers to a polymer of nucleotides, or analogs thereof, of any length, including oligonucleotides that range from 10-100 nucleotides in length and polynucleotides of greater than 100 nucleotides in length. The term "polypeptide" refers to a polymer of amino acids of any length, including peptides that range from 6-50 amino acids in length and polypeptides that are greater than about 50 amino acids in length.

In most embodiments, the terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids. The term "fusion protein" or grammatical equivalents thereof references a protein composed of a plurality of polypeptide components, that while not attached in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length.

In certain embodiments, variants of amino acid and nucleic acid sequences include "conservatively modified variants." With respect to particular nucleic acid sequences, conservatively modified variants may refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

By way of example, the following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (V);
7) Serine (S), Threonine (T); and
8) Cysteine (C), Methionine (M)
(see, e.g., Creighton, Proteins (1984)).

As recognized by those of skill in the art, macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part L' The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of (β-sheet and α-helices. "Tertiary structure" refers to the complete three dimensional structure of a polypeptide monomer. "Quaternary structure" refers to the three dimensional structure formed by the non-covalent association of independent tertiary units. Anisotropic terms are also known as energy terms.

The terms "identical" or percent "identity," in the context of two or more nucleic acids or polypeptide sequences, may refer to two or more sequences or subsequences or domains that are the same or have a specified percentage of amino acid residues or nucleotides that are the same (i.e., 50% identity, optionally 55%, 60%, 65%, 70%, 75%, 80%, 85%, 90%, 95% or higher identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. By way of example, when using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 21 S:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSLTM62 scoring matrix (see Henikoff & Henikoff, Proc. Natl. Acad. Sci. USA 89:10915 (1989)) alignments (B) of 50, expectation (E) of 10, $M=5$, $N=-4$, and a comparison of both strands.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences: This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighty end gaps. PILEUP can be obtained from the GCG sequence analysis software package, e.g., version 7.0 (Devereaux et al., *Nuc. Acids Res.* 12:387-395 (1984)).

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" may refer to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" may refer to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridisation with Nucleic Probes, "Overview of principles of hybridization and the strategy of nucleic acid assays"* (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, S×SSC, and 1% SDS, incubating at 42° C., or, S×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions may still substantially identical if the polypeptides which they encode are substantially identical. This occurs, for example, when a copy of a nucleic acid is created using the maximum codon degeneracy permitted by the genetic code.' In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

The term "capture agent" refers to an agent that binds an analyte through an interaction that is sufficient to permit the agent to bind and concentrate the analyte from a homogeneous mixture of different analytes. The binding interaction may be mediated by an affinity region of the capture agent. Representative capture agents include polypeptides and polynucleotides, for example antibodies, peptides or fragments of single stranded or double stranded DNA may employed. Capture agents usually "specifically bind" one or more analytes.

Accordingly, the term "capture agent" refers to a molecule or a multi-molecular complex which can specifically bind an analyte, e.g., specifically bind an analyte for the capture agent, with a dissociation constant ($K_D$) of less than about $10^{-6}$ M.

The term "specific binding" refers to the ability of a capture agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold). In certain embodiments, the affinity between a capture agent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, usually less than about $10^{-10}$ M.

The term "capture agent/analyte complex" is a complex that results from the specific binding of a capture agent with an analyte, i.e., a "binding partner pair". A capture agent and an analyte for the capture agent specifically bind to each other under "conditions suitable for specific binding", where such conditions are those conditions (in terms of salt concentration, pH, detergent, protein concentration, temperature, etc.) which allow for binding to occur between capture agents and analytes to bind in solution. Such conditions, particularly with respect to proteins, are well known in the art (see, e.g., Harlow and Lane (*Antibodies: A Laboratory Manual Cold Spring Harbor Laboratory*, Cold Spring Harbor, N.Y. (1989)). Conditions suitable for specific binding typically permit capture agents and target pairs that have a dissociation constant ($K_D$) of less than about $10^{-6}$ M to bind to each other, but not with other capture agents or targets.

As used herein, "binding partners" and equivalents refer to pairs of molecules that can be found in a capture agent/analyte complex, i.e., exhibit specific binding with each other.

The phrase "surface-bound capture agent" refers to a capture agent that is immobilized on a surface of a solid substrate, where the substrate can have a variety of configurations, e.g., a sheet, bead, or other structure, such as a plate with wells. In certain embodiments, the collections of capture agents employed herein are present on a surface of the same support, e.g., in the form of an array.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "fusion protein" or grammatical equivalents thereof is meant a protein composed of a plurality of polypeptide components, that while typically unjoined in their native state, typically are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing binding" includes determining the amount of binding, and/or determining whether binding has occurred (i.e., whether binding is present or absent).

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a COX-2 modulator that can provide for enhanced or desirable effects in the subject (e.g., beneficial increase in a physiological parameter of the subject, reduction of disease symptoms, decreased pain sensation or decreased inflammation, decreased side effects of another COX-2 inhibitor, etc.).

"Subject", "individual," "host" and "patient" are used interchangeably herein, to refer to an animal, human or non-human, susceptible to or having a COX-2 amenable to therapy according to the methods of the invention. Generally, the subject is a mammalian subject. Exemplary subjects include, but are not necessarily limited to, humans, non-human primates, mice, rats, cattle, sheep, goats, pigs, dogs, cats, and horses, with humans being of particular interest.

Various biochemical and molecular biology methods referred to herein are well known in the art, and are described in, for example, Sambrook et al., *Molecular Cloning: A Laboratory Manual*, Cold Spring Harbor Press, N.Y. Second (1989) and Third (2000) Editions, and *Current Protocols in Molecular Biology*, (Ausubel, F. M. et al., eds.) John Wiley & Sons, Inc., New York (1987-1999).

The invention provides an assay for determining whether a test agent is a COX modulator. In general terms, the assay includes: determining whether a test agent modulates binding of a PDZ-containing polypeptide to a PL-containing polypeptide, e.g., a COX-2 PL containing polypeptide. The PDZ-containing polypeptide may contain the PDZ domain of, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2. The assays may be done in a cell-free environment or in a cellular environment, particularly using a neuronal cell. The invention finds use in a variety of therapeutic applications, including for identifying agents for use in treating pain, cancer, inflammation and neuronal conditions caused by acute insult, e.g., stroke.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

II. Assays, Modulators, and Methods

As noted above, the invention provides a variety of assays for identifying modulators of COX-2 and PDZ ligand binding modulators, e.g., COX-2 PDZ ligand binding modulators. In general, the methods involve testing binding of a PDZ ligand polypeptide, including COX-2 PDZ ligand polypeptides, to a polypeptide having a PDZ domain in the presence of a test agent (i.e., candidate drug compound). A test agent that modulates binding between the PDZ ligand polypeptide and a polypeptide having a PDZ domain modulates (i.e., increases or decreases, including abolishes) binding between the two proteins. As will be described below, binding between the two polypeptides may be assessed using a variety of means. Also as will be described in greater detail below, the assay may be performed in a cell-free environment (i.e., "in vitro") using isolated polypeptides. In certain embodiments, the assay may be a cellular assay in which binding of the polypeptides within a cell, in the presence of a test agent, is evaluated. A wide variety of assay platforms are therefore available.

Binding of the polypeptides may be assayed using methods that are well known in the art. For example, binding may be assayed biochemically, or, in other embodiments, the two proteins may be assayed by detecting a signal that is only produced when the proteins are bound together. In testing candidate agents, such a signal can be evaluated in order to assess binding between the two proteins. For example, as used in the subject assays, the polypeptides may form a fluorescence resonance energy transfer (FRET) system, bioluminescence resonance energy transfer (BRET) system, or calorimetric signal producing system that can be assayed.

The assay, whether it is performing in vitro or in a cellular environment, generally involves a) a polypeptide including the PDZ ligand and b) a polypeptide including a PDZ domain from, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2. In many embodiments, at least one of the polypeptides may be a fusion protein that facilitates detection of binding between the polypeptides. Accordingly, one of the polypeptides may contain, for example, an affinity tag domain or an optically detectable reporter domain.

Suitable affinity tags include any amino acid sequence that may be specifically bound to another moiety, usually another polypeptide, most usually an antibody. Suitable affinity tags include epitope tags, for example, the V5 tag, the FLAG tag, the HA tag (from hemagglutinin influenza virus), the myc tag, etc. Suitable affinity tags also include domains for which, binding substrates are known, e.g., HIS, GST and MBP tags, etc., and domains from other proteins for which specific binding partners, e.g., antibodies, particularly monoclonal antibodies, are available. Suitable affinity tags also include any protein-protein interaction domain, such as a IgG Fc region, which may be specifically bound and detected using a suitable binding partner, e.g., the IgG Fc receptor.

Suitable reporter domains include any domain that can optically report the presence of a polypeptide, e.g., by emitting light or generating a color. Suitable light emitting reporter domains include luciferase (from, e.g., firefly, Vargula, *Renilla reniformis* or *Renilla muelleri*), or light emitting variants thereof. Other suitable reporter domains include fluorescent proteins, (from e.g., jellyfish, corals and other coelenterates as such those from *Aequoria, Renilla, Ptilosarcus, Stylatula* species), or light emitting variants thereof. Light emitting variants of these reporter proteins are very well known in the art and may be brighter, dimmer, or have different excitation and/or emission spectra, as compared to a native reporter protein. For example, some variants are altered such that they no longer appear green, and may appear blue, cyan, yellow, enhanced yellow red (termed BFP, CFP, YFP eYFP and RFP, respectively) or have other emission spectra, as is known in the art. Other suitable reporter domains include domains that can report the presence of a polypeptide through a biochemical or color change, such as β-galactosidase, β-glucuronidase, chloramphenicol acetyl transferase, and secreted embryonic alkaline phosphatase. In some preferred embodiments, the reporter domain is *Renilla* luciferase (e.g., pRLCMV; Promega, catalog number E2661).

Also as is known in the art, an affinity tag or a reporter domain may be present at any position in a polypeptide of interest. However, in certain embodiments, they are present at the C- or N-terminal end of a polypeptide.

In particular embodiments, one or both of the polypeptides may contain a tag or reporter. For example, if FRET or BRET methods are employed, the polypeptides may both be tagged using different autofluorescent polypeptides.

In certain embodiments, the PDZ domain-containing polypeptide includes at least the PDZ domain from SHANK1, SHANK2 or SHANK3, which PDZ domains each bind to the PDZ ligand of COX-2. The SHANK PDZ domain may contain the PDZ domain of a "wild-type" SHANK polypeptide, or a variant thereof that retains ability to bind to the PDZ ligand of COX-2. The sequence of the PDZ domains for wild-type SHANK1, SHANK2 or SHANK3 are illustrated in FIG. 1A. Any length of PDZ domain, including the minimum, intermediate and +10 lengths shown in FIG. 1A, may be employed herein.

The SHANK1 and SHANK2 and SHANK3 PDZ domain polypeptides and encoding cDNAs are deposited in the GenBank database as GID NOS: 7025450 and 6049185, respectively, whereas the coding sequence for SHANK3 is encoded by GenBank accession no. XM_037493 (GI: 51476100).

In other embodiments, the PDZ domain-containing polypeptide may include at least the PDZ domain from MAST2, which PDZ domain generally binds to the PDZ ligand of COX-2. The MAST2 PDZ domain may contain the PDZ domain of a "wild-type" MAST2 polypeptide, or a variant thereof that retains ability to bind to the PDZ ligand of COX-2. The MAST2 PDZ domain polypeptide and encoding cDNA are deposited in the GenBank database as accession no. AB047005.

In other embodiments, the PDZ domain-containing polypeptide may include at least the PDZ domain from MAGI1, including MAGI1 d1, which PDZ domains generally bind to the PDZ ligand of COX-2. The MAGI1 PDZ domains may contain the PDZ domain of a "wild-type" MAGI1 d1 polypeptide, or a variant thereof that retains ability to bind to the PDZ ligand of COX-2. The MAGI1 d1 PDZ domain polypeptide and encoding cDNA are deposited in the GenBank database as accession no. Q96QZ7

In other embodiments, the PDZ domain-containing polypeptide may include at least the PDZ domain from TIP-1, which PDZ domain generally binds to the PDZ ligand of COX-2. The TIP-1 PDZ domain may contain the PDZ domain of a "wild-type" TIP-1 polypeptide, or a variant thereof that retains ability to bind to the PDZ ligand of COX-2. The TIP-1 PDZ domain polypeptide and encoding cDNA are deposited in the GenBank database as accession no. AF028823.

In other embodiments, the PDZ domain-containing polypeptide may include at least the PDZ domain from PSD95, including PSD95 d1, PSD95 d2, and PSD95 d3, which PDZ domains generally bind to the PDZ ligand of COX-2. The PSD95 PDZ domains may contain the PDZ domain of a "wild-type" PSD95 polypeptide, or a variant thereof that retains ability to bind to the PDZ ligand of COX-2. The PSD95 PDZ domain polypeptides and encoding cDNA are deposited in the GenBank database as accession no. AAC52113.

In certain embodiments, the COX-2 PDZ ligand-containing polypeptide contains at least the PDZ ligand of COX-2, or a variant or fragment thereof. The COX-2 PDZ ligand may contain the PDZ ligand of a "wild-type" COX-2 polypeptide, or a variant or fragment thereof that retains ability to bind to a PDZ domain, e.g., a domain of a MAGI1 (including MAGI1 d1), TIP-1, SHANK (including SHANK1, SHANK2, and SHANK3), PSD95 (including PSD95 d1, PSD95 d2, and PSD95 d3) or MAST2 polypeptide.

The sequence of a wild-type COX-2 PDZ ligand is illustrated in FIG. 1A, including several variants thereof. Any combination of the indicated variants are envisioned, as well as conservatively modified variants thereof. For instance, the COX-2 PDZ ligand polypeptides of the invention may comprise a PL region having at least 50% identity, optionally at least 55%, at least 60%, at least 65%, at least 70%, at least 75%, at least 80%, at least 85%, at least 90%, at least 95% or more identity to SEQ. ID NO.: 13. Further, any length COX-2 PDZ ligand polypeptide may be used, which retains its ability to bind a PDZ domain. For instance, COX-2 PDZ polypeptides having a total length of at least about, e.g., 30, 28, 26, 25, etc., amino acids, and comprising a PL region having, e.g., a fragment of 5 contiguous amino acids, 6 contiguous amino acids, 7 contiguous amino acids, 8 contiguous amino acids or 9 contiguous amino acids of SEQ. ID NO.: 13, or a variant thereof that retains its ability to bind to a PDZ domain.

In another embodiment, the PDZ ligand-containing polypeptide may including the putative PDZ ligand of COX- 1. The COX-1 PDZ ligand may contain the PDZ ligand of a "wild-type" COX-1 polypeptide, or a variant or fragment thereof that retains ability to bind to a PDZ domain, e.g., of a MAGI1 (including MAGI1 d1), TIP-1, SHANK (including SHANK1, SHANK2, and SHANK3), PSD95 (including PSD95 d1, PSD95 d2, and PSD95 d3) or MAST2 polypeptide. The sequence of a "wild-type" COX-1 PDZ ligand is generally AVERPSTEL (SEQ. ID NO.: 93), and may be employed herein. Conservatively modified variants thereof and fragments are envisioned as well. For instance, the COX-1 PDZ ligand polypeptides of the invention may comprise a PL region having at least 50% identity, optionally at least 55%, at least 60%, at least 65%, at least 70%, at least 75%, at least 80%, at least 85%, at least 90%, at least 95% or more identity to SEQ. ID NO.: 93. Further, any length COX-1 PDZ ligand polypeptide may be used, which retains its ability to bind a PDZ domain. For instance, COX-1 PDZ polypeptides having a total length of at least about, e.g., 30, 28, 26, 25, etc., amino acids, and comprising a PL region having, e.g., a fragment of 5 contiguous amino acids, 6 contiguous amino acids, 7 contiguous amino acids, 8 contiguous amino acids or 9 contiguous amino acids of SEQ. ID NO.: 93, or a variant thereof that retains its ability to bind to a PDZ domain.

Variant polypeptides are readily designed since the PDZ domain is well characterized at the structural level. For example, the three-dimensional structure of the PDZ domain is described and discussed in great detail in Doyle (Cell 1996 95:1067-1076) and the structure of, e.g., SHANK1 bound to the PDZ ligand domain of guanylate kinase-associated protein (GKAP1a) has been determined by crystallography. Variants are generally at least 80% identical, at least 90% identical, at least 95% identical or, in certain embodiments at least 98% or at least 99% identical to a wild-type PDZ domain amino acid sequence. In other words, as employed in a method described herein, a PDZ domain-containing polypeptide may contain at least 1, 2, 3, 4, or 5 or more and in certain embodiments up to 10 amino acid substitutions, as compared to a wild-type sequence. A substitution may be conservative (i.e., replacing one amino acid with another within the following groups: gly, ala; val, ile, leu; asp, glu; asn, gln; ser, thr; lys, arg; and phe, tyr), or non-conservative. By way of example, since each of the SHANK PDZ domains bind COX-2 and are highly similar in sequence (the SHANK1 and SHANK2 PDZ domains are approximately 85%, the SHANK1 and SHANK3 PDZ domains are approximately 79% identical and the SHANK3 and SHANK3 PDZ domains are approximately 80% identical), amino acids may be readily substituted from one sequence to another without losing the ability to bind to COX-2. Exemplary amino acid substitutions that could be made in the subject polypeptides are illustrated in FIG. 1B and FIG. 2. In other words, since all the polypeptides shown in FIG. 1B bind to the same PDZ ligand, amino acids at the same position within each of the polypeptides may be substituted without significant loss of binding activity. The PDZ domain of the polypeptides employed in the instant methods may be longer or shorter by up to 10 or more amino acids than the polypeptides illustrated in FIG. 1B.

When a particular PDZ domain-containing polypeptide is referenced herein, e.g., when a reference is made to a MAGI1, TIP-1, PSD95, SHANK1, SHANK2, SHANK3 or MAST2 PDZ domain-containing polypeptide, the reference is intended to encompass polypeptides containing a wild-type PDZ domain, and variants or fragments thereof that retain PDZ ligand binding activity, e.g., COX-1 or COX-2 PL binding activity.

When a particular PDZ ligand-containing polypeptide is referenced herein, e.g., when a reference is made to a COX-2 PDZ ligand-containing polypeptide or COX-2 PDZ ligand-containing polypeptide, the reference is intended to encompass polypeptides containing a wild-type PDZ ligand, and variants and fragments thereof that retain PDZ domain binding activity.

Such polypeptides may be made synthetically (i.e., using a machine) or using recombinant means, as is known in the art. Methods and conditions for expression of recombinant proteins are well known in the art. See, e.g., Sambrook, supra, and Ausubel, supra. Typically, polynucleotides encoding the polypeptides used in the invention are expressed using expression vectors. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells. Typically, DNA encoding a polypeptide of the invention is inserted into DNA constructs capable of introduction into and expression in an in vitro host cell, such as a bacterial (e.g., *E. coli, Bacillus subtilis*), yeast (e.g., *Saccharomyces*), insect (e.g., *Spodoptera frugiperda*), or mammalian cell culture systems. Mammalian cell systems are preferred for many applications. Examples of mammalian cell culture systems useful for expression and production of the polypeptides of the present invention include human embryonic kidney line (293; Graham et al., 1977, *J. Gen. Virol.* 36:59); CHO (ATCC CCL 61 and CRL 9618); human cervical carcinoma cells (HeLa, ATCC CCL 2); and others known in the art. The use of mammalian tissue cell culture to express polypeptides is discussed generally in Winnacker, *From Genes to Clones* (VCH Publishers, N.Y., N.Y., 1987) and Ausubel, supra. In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

As noted above, the subject assay may be performed in vitro (i.e., in which the polypeptides are present in a solution a not in a cell) or in a cellular environment (in which the polypeptides are present in a cell).

III. In Vitro Assays

In vitro assays may be performed using a wide variety of platforms that are well known in the art. In certain embodiments, the methods involve linking, either covalently or non-covalently, a first polypeptide (either the PDZ domain polypeptide or the PDZ ligand polypeptide) to a substrate, contacting the substrate-bound polypeptide with the second polypeptide, and detecting the presence of the second polypeptide. In other embodiments, the first and second polypeptides are not substrate-bound, and the assay is performed in solution. The method may be performed in the presence of a test agent. In embodiments in which one of the polypeptides are detectably labeled (e.g., as an optically-detectable fusion protein), the presence of the labeled polypeptide is detected by detecting the label.

A substrate contains a solid, semi-solid, or insoluble support and is made from any material appropriate for linkage to a polypeptide, and does not interfere with the detection method used. As will be appreciated by those in the art, the number of possible affinity substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, ceramics, and a variety of other polymers. In one embodiment, the substrates allow optical detection and do not themselves appreciably fluoresce or emit light. In addition, as is known the art, the substrate may be coated with any number of materials, including polymers, such as dextrans, acrylamides, gelatins, agarose, biocompatible substances such as proteins including bovine and other mammalian serum albumin.

In certain embodiments, the substrate is coated in an agent that facilitates the specific binding (either directly or indirectly) of a polypeptide to the substrate. For example, the substrate is coated in streptavidin, and can bind a biotinylated polypeptide with affinity to the polypeptide of interest. In another example, the substrate is directly or indirectly (e.g., through protein A) coated with an antibody specific for the polypeptide.

As mentioned above, after the first polypeptide is linked to the substrate, the second polypeptide is contacted with the substrate and maintained under conditions suitable for specific binding of the second polypeptide to the first polypeptide, typically in the presence of a test agent. The second polypeptide is only detectable on the substrate only if the first and second polypeptides form a complex. Detection of the second polypeptide indicates that the first and second polypeptides form a complex. Detection of the second polypeptide that is bound to the affinity substrate is carried out directly (while the second polypeptide is bound to the substrate), or indirectly (e.g., after elution of the polypeptide from the substrate).

In embodiments where the second polypeptide contains a reporter domain, the second polypeptide may be detected by detecting reporter activity. Methods of determining reporter activity, e.g., luciferase and GFP activity, are generally well known in the art (e.g., Ramsay et al., *Br. J. Pharmacology*, 2001, 133:315-323), and need not be described any further. Detection of the second polypeptide may also be accomplished using an antibody, e.g., a labeled antibody. Methods for detecting polypeptides using antibodies are also well known in the art (e.g., Ausubel et al., *Short Protocols in Molecular Biology*, 3rd ed., Wiley & Sons, 1995; and Harlow et al., *Antibodies: A Laboratory Manual*, First Edition 1988 Cold Spring Harbor, N.Y.) and need not be described in more detail.

Fluorescence Resonance Energy Transfer (FRET) and Bioluminescence Resonance Energy Transfer (BRET) systems may also be employed, as generally understood by those skilled in the art. Such systems are described in further detail below with reference to cell based assays.

In order to determine whether a test agent modulates binding between the subject polypeptides, the above assay may be performed in the presence or absence of a test agent.

Two complementary assays, termed "A" and "G" (or a modified "G" assay), were developed to detect binding between a PDZ-domain polypeptide and candidate PDZ ligand. In each of the two different assays, binding is detected between a peptide having a sequence corresponding to the C-terminus of a protein anticipated to bind to one or more PDZ domains (i.e., a candidate PL peptide) and a PDZ-domain polypeptide (typically a fusion protein containing a PDZ domain). In the "A" assay, the candidate PL peptide is immobilized and binding of a soluble PDZ-domain polypeptide to the immobilized peptide is detected (the "A" assay is named for the fact that in one embodiment an avidin surface is used to immobilize the peptide). In the "G" assay, the PDZ-domain polypeptide is immobilized and binding of a soluble PL peptide is detected (the "G" assay is named for the fact that in one embodiment a GST-binding surface is used to immobilize the PDZ-domain polypeptide). However, it will be appreciated by ordinarily skilled practitioners that these assays can be modified in numerous ways while remaining useful for the purposes of the present invention.

Details of the A and G assays are set forth in the Examples section below, and in U.S. patent application Ser. No. 10/630,590, filed Jul. 29, 2003 and published as US20040018487.

IV. Cellular Assays

Cellular assays generally involve co-producing (i.e., producing in the same cell, regardless of the time at which they are produced), the subject polypeptides using recombinant DNA. Suitable cells for producing the subject polypeptides include prokaryotic, e.g., bacterial cells, as well as eukaryotic cells e.g., an animal cell (for example an insect, mammal, fish, amphibian, bird or reptile cell), a plant cell (for example a maize or *Arabidopsis* cell), or a fungal cell (for example a *S. cerevisiae* cell). Any cell suitable for expression of subject polypeptide-encoding nucleic acid may be used as a host cell. Usually, an animal host cell line is used, examples of which are as follows: monkey kidney cells (COS cells), monkey kidney CVI cells transformed by SV40 (COS-7, ATCC CRL 165 1); human embryonic kidney cells (HEK-293, Graham et al., *J. Gen Virol.* 36:59 (1977)); HEK-293T cells; baby hamster kidney cells (BHK, ATCC CCL 10); chinese hamster ovary-cells (CHO, Urlaub and Chasin, *Proc. Natl. Acad. Sci.* (USA) 77:4216, (1980); mouse sertoli cells (TM4, Mather, *Biol. Reprod.* 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., *Annals N.Y. Acad. Sci* 383:44-68 (1982)); NIH/3T3 cells (ATCC CRL-1658); and mouse L cells (ATCC CCL-1).

In particular embodiments, neuronal cells, e.g., SHSY5Y (neuroblastoma cell line), hippocampal murine HT-22 cells, primary cultures from astrocytes, cerebral cortical neuronal-astrocytic co-cultures, mixed neuronal/glial hippocampal cultures, cerebellar granular neuronal cell cultures or primary neuronal cultures derived from rat cortex (E15-17) may be employed.

Additional cell lines will become apparent to those of ordinary skill in the art. A wide variety of cell lines are available from the American Type Culture Collection, 10801 University Boulevard, Manassas, Va. 20110-2209.

Again, a wide variety of platforms may be employed to detect binding between the subject polypeptides in a cell. For example, so-called "two-hybrid" methods may be employed, or a wide variety of fluorescence-based methods, e.g., FRET or BRET-based methods. In general, these methods involve contacting a cell that produces the subject polypeptides with a test agent, and determining if the test agent has any effect on binding between the subject polypeptides.

In one embodiment, the GAL4 system is used to screen agents that modulate binding between the subject polypeptides. Such methods may employ a vector (or vector system) encoding two polypeptides: a DNA binding domain polypeptide that contains either a PDZ domain or a PDZ ligand and DNA activation domain polypeptide containing the region not in the DNA binding domain polypeptide. The interaction between the PDZ domain and the PDZ ligand activates the expression of a reporter gene or selectable marker. The levels of α- or β-galactosidase, β-lactamase are measured by quantifying their enzymatic activity using calorimetric substrates, such as orthomethylphenylthiogalactoside (OMTP) or X-gal; the levels of light, e.g., fluorescence, may be assessed photometrically, e.g., fluorometrically. Pools of agents or individual agents are added to cultures in wells and the levels of inhibition or facilitation of the interaction by the agents are determined from the levels of the reporter gene activity. Such methods are very well known in the art.

In another exemplary embodiment, Fluorescence Resonance Energy Transfer (FRET) may be used to detect binding between two polypeptides in a cell. Fluorescent molecules having the proper emission and excitation spectra that are brought into close proximity with one another can exhibit FRET. The fluorescent molecules are chosen such that the emission spectrum of one of the molecules (the donor molecule) overlaps with the excitation spectrum of the other molecule (the acceptor molecule). The donor molecule is excited by light of appropriate intensity within the donor's excitation spectrum. The donor then emits the absorbed energy as fluorescent light. The fluorescent energy it produces is quenched by the acceptor molecule. FRET can be manifested as a reduction in the intensity of the fluorescent signal from the donor, reduction in the lifetime of its excited state, and/or re-emission of fluorescent light at the longer wavelengths (lower energies) characteristic of the acceptor. When the fluorescent proteins physically separate, FRET effects are diminished or eliminated. (See, U.S. Pat. No. 5,981,200, the disclosure of which is hereby incorporated by reference in its entirety.)

For example, a cyan fluorescent protein is excited by light at roughly 425-450 nm wavelength and emits light in the range of 450-500 nm. Yellow fluorescent protein is excited by light at roughly 500-525 nm and emits light at 525-500 nm. If these two proteins are present in a cell but not in close proximity, the cyan and yellow fluorescence may be separately visualized. However, if these two proteins are forced into close proximity with each other, the fluorescent properties will be altered by FRET. The bluish light emitted by CFP will be absorbed by YFP and re-emitted as yellow light. FRET is typically monitored by measuring the spectrum of emitted light in response to stimulation with light in the excitation range of the donor and calculating a ratio between the donor-emitted light and the acceptor-emitted light. When the donor: acceptor emission ratio is high, FRET is not occurring and the two fluorescent proteins are not in close proximity. When the donor: acceptor emission ratio is low, FRET is occurring and the two fluorescent proteins are in close proximity. In this manner, the interaction between a first and second polypeptide fused to a first and second reactive module, wherein the first and second reactive modules are donor and acceptor fluorescent molecules, respectively, may be measured. As such, the two polypeptides may contain a system that provides for FRET, e.g., one polypeptide contains GFP whereas the other contains YFP.

In a further embodiment, the first and seconds provide a Bioluminescence Resonance Energy Transfer (BRET) system. In such a system, one polypeptide of interest produces (or destroys) a fluorescent product (or substrate) and the other polypeptide of interest is a fluorescent protein that undergoes resonant energy transfer with the fluorescent product (or substrate). In one embodiment, a BRET system comprises a luciferase from *Renilla* and a GFP. Exemplary BRET methodologies are described in Kroeger et al., *J Biol. Chem.* 2001 Apr. 20; 276(16):12736-43 and Xu et al., *Proc Natl Acad Sci USA*. 1999 Jan. 5; 96(1):151-6.

A variety of colorimetric signal producing systems may also be employed.

The test agents employed in the subject methods may be any type of compound. The candidate agents or test compounds may be any of a large variety of compounds, both naturally occurring and synthetic, organic and inorganic, and including polymers (e.g., oligopeptides, polypeptides, oligonucleotides, and polynucleotides), small molecules (i.e., under about 500 Da in weight), antibodies, sugars, fatty acids, nucleotides and nucleotide analogs, analogs of naturally occurring structures (e.g., peptide mimetics, nucleic acid analogs, and the like), and numerous other compounds. In certain embodiment, test agents are prepared from diversity libraries, such as random or combinatorial peptide or non-peptide libraries. Many libraries are known in the art that can be used, e.g., chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; PCT Publication No. WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science*, 249:404-406; Christian, R. B., et al., 1992, *J. Mol. Biol.* 227:711-718); Lenstra, 1992, *J. Immunol. Meth.* 152:149-157; Kay et al., 1993, *Gene* 128:59-65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, *Proc. Natl. Acad. Sci. USA* 91:9022-9026. By way of examples of non-peptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

In certain embodiments, the test agent may be a COX-2 selective inhibitor of prostaglandin synthesis, e.g., a diarylheterocycle (including celecoxib and rofecoxib), an acidic sulfonamide, an indomethacin analog, a zomepirac analog, a chromene analog or a di-t-butylphenol. For example, COX-2 inhibitory oxazoles are described in U.S. Pat. No. 5,380,738, COX-2 inhibitory cyclopentenes are described in U.S. Pat. No. 5,344,991, COX-2 inhibitory spiro are described in U.S. Pat. No. 5,393,790, COX-2 inhibitory thiophene and furan derivatives are described in WO94/15932 and COX-2 inhibitory pyrazolyl sulfonamide derivatives are described in U.S. WO95/15316. The subject method may find particular use as a counterscreen to identify inhibitors of COX-2 (e.g., inhibitors that reduce prostaglandin synthesis) that do, or do not, also modulate binding between COX-2 and the PDZ-containing proteins.

In other embodiments, test agent may be a PDZ domain, or an analog thereof, a COX-2 PDZ ligand or analog thereof, or a non-COX-2 PDZ ligand that binds to the PDZ domain or, e.g., MAGI1, TIP-1, PSD95, SHANK or MAST2 (e.g., as illustrated in FIGS. 5A and 5B).

Once identified as an agent that modulates binding of COX-2 to a PDZ-containing polypeptide, i.e., a COX-2 PDZ ligand binding modulator, the agent may be tested in a variety of different assays, including cell-free assays, cellular assays and assays that employ animals or brain sections ("ex vivo" brain sections). For example, the binding-modulatory agent may be tested to determine if the agent modulates cycloxidase activity, prostaglandin synthesis, NMDA receptor activation, iNOS induction, pain, inflammation, COX-2 induction, COX-2 activity or nitric oxide levels, anti-tumor activity assays, anti-cellular proliferation assays, etc., in any appropriate system.

In particular embodiments, a binding-modulatory agent is tested to determine if it provides protection against acute insult (e.g., hypoxia or ischemia) or aid cell recovery after an insult. Such assays may be performed in a variety of platforms, including, but not limited to: cultured neurons (see, e.g., Shibuta, *J. Neurol. Sci.* 2003 215:31-6, and Lee *Neurochem. Int.* 2004 44:107-18), ex vivo brain slices, e.g., organotypic hippocampal slice cultures (see e.g., Barth et al., *Exp. Brain Res.* 2005 161:351-7, and Saransaari, *Neurochem. Res.* 2004 29:1511-8), and animals (see, e.g., Lee *J., Neurosci. Res.* 2004 77:892-900; Vannucci, *Ann. N.Y. Acad. Sci.* 1997 835:234-49). Such assays are generally well known in the art.

V. Binding-Modulatory Compounds

In addition to the assays set forth above, the invention also provides a variety of modulatory compounds that may be used as PDZ-inhibitors based on their general ability to bind PDZ domains, and to disrupt PDZ/PL interactions relevant to various disease conditions or disorders, as recognized in the art. For instance, the modulatory compounds may be employed as inhibitors of binding between COX-2 and a PDZ-containing polypeptide in a cell, both in vitro and in vivo.

In certain embodiments, the inhibitory compounds are structurally related to the PDZ domains of MAGI1 (including MAGI1 d1), TIP-1, SHANK (including SHANK1, SHANK2, and SHANK3), PSD95 (including PSD95 d1, PSD95 d2, and PSD95 d3) or MAST2, such as those shown in FIGS. 1A and 2B, and either contain the wild-type amino acid sequence of the PDZ domain or a variant thereof that retains COX-2 binding activity. Such polypeptides may be employed to compete with a full-length PDZ peptide, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2 peptide, for binding to COX-2 in a cell.

In other embodiments, the inhibitory compounds are structurally related to the PDZ ligand of COX-1 or COX-2, such as those shown in FIG. 1A and SEQ. ID NO.: 93, and either contain the wild-type amino acid sequence of the PL, or is a variant or fragment thereof that retains it ability to bind to a PDZ domain, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2 binding activity. In certain embodiments, the COX PLs may includes a transporter peptide, such as but not limited to a Tat transporter peptide sequence (e.g., YGRKKRRQRRR, SEQ. ID NO.: 94, from peptide 1956, SEQ. ID NO.: 15). Such transporter peptides may act to facilitate transport into a cell following administration in vivo, and optionally to enhance binding to the PDZ domain. Further, such polypeptides may be employed to compete with full-length COX-2 for binding to a PDZ peptide, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2, in a cell.

In other embodiments, the inhibitory compounds are structurally related to the PDZ ligand of other PDZ-ligand containing polypeptides that bind to the PDZ domain of, e.g., MAGI1 (including MAGI1 d1), TIP-1, SHANK (including SHANK1, SHANK2, and SHANK3), PSD95 (including PSD95 d1, PSD95 d2, and PSD95 d3) or MAST2. The sequences of several exemplary PDZ ligands that bind to such PDZ peptides are shown in FIGS. 5A and 5B, and either contain the wild-type amino acid sequence of PDZ ligand or a variant thereof that retains SHANK1, SHANK2, SHANK3 or MAST2 binding activity. Such polypeptides may be employed to compete with full-length COX-2 for binding to SHANK1, SHANK2, SHANK3 or MAST2 in a cell. It is understood that for any peptide or mimetic thereof based on the sequence of a PDZ ligand, the sequence at the extreme C-terminus of the polypeptide may be any of the following sequences: TEL, SEL, TRL, SRL, SAL, TKL, SKL, SKI, TKI, SRI, TRI, SDL, SDI or TDI.

In particular embodiments, the inhibitor compound may be a mimetic of a subject PDZ domain or PDZ ligand, i.e., a synthetic chemical compound that has substantially the same structural and/or functional characteristics as a subject PDZ domain or PDZ ligand. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation will determine whether a mimetic is within the scope of the invention, i.e., that its structure and/or function is not substantially altered. Thus, a mimetic composition is within the scope of the invention if it is capable of inhibiting binding between the subject polypeptides.

Mimetics can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=-dicyclohexylcarbodiimide (DCC) or N,N=-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, *A Peptide Backbone Modifications*, Marcell Dekker, NY).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R=N=C=N=R=) such as, e.g., 1-cyclohexyl-3(2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines, to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

An amino acid of a subject polypeptide can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) *Tet. Lett.* 26:647-650; Feigl (1986) *J. Amer. Chem. Soc.* 108:181-182; Kahn (1988) *J. Amer. Chem. Soc.* 110:1638-1639; Kemp (1988) *Tet. Lett.* 29:5057-5060; Kahn (1988) *J. Molec. Recognition* 1:75-79. Beta sheet mimetic structures have been described, e.g., by Smith (1992) *J. Amer. Chem. Soc.* 114:10672-10674. For example, a type VI beta turn induced by a cis amide surrogate, 1,5-disubstituted tetrazol, is described by Beusen (1995) *Biopolymers* 36:181-200. Incorporation of achiral omega-amino acid residues to generate polymethylene units as a substitution for amide bonds is described by Banerjee (1996) *Biopolymers* 39:769-777. Secondary structures of polypeptides can be analyzed by, e.g., high-field 1H NMR or 2D NMR spectroscopy, see, e.g., Higgins (1997) *J. Pept. Res.* 50:421-435. See also, Hruby (1997) *Biopolymers* 43:219-266, Balaji, et al., U.S. Pat. No. 5,612,895.

The subject compounds may be further modified to make the compound more soluble or to facilitate its entry into a cell. For example, the compound may be PEGylated at any position, or the compound may contain a transmembrane transporter region.

A number of peptide sequences have been described in the art as capable of facilitating the entry of a peptide linked to these sequences into a cell through the plasma membrane (Derossi et al., 1998, *Trends in Cell Biol.* 8:84). For the purpose of this invention, such peptides are collectively referred to as transmembrane transporter peptides. Examples of these peptide include, but are not limited to, tat derived from HIV (Vives et al., 1997, *J. Biol. Chem.* 272:16010; Nagahara et al., 1998, *Nat. Med.* 4:1449), antennapedia from Drosophila (Derossi et al., 1994, *J. Biol. Chem.* 261:10444), VP22 from herpes simplex virus (Elliot and D'Hare, 1997, *Cell* 88:223-233), complementarity-determining regions (CDR) 2 and 3 of anti-DNA antibodies (Avrameas et al., 1998, *Proc. Natl. Acad. Sci. U.S.A.*, 95:5601-5606), 70 KDa heat shock protein (Fujihara, 1999, *EMBO J.* 18:411-419) and transportan (Pooga et al., 1998, *FASEB J.* 12:67-77). In certain embodiments, a truncated HIV tat peptide may be employed.

In yet other embodiments, the inhibitory compounds may be a small molecule compound that inhibits the PDZ/PL interaction, e.g., though binding of a PDZ domain. Exemplary small molecule compounds include COX-2 inhibitors, such as but not limited to, niflumic acid, ibuprofen, naproxen sodium, diclofenac sodium salt, acetylsalicyclic acid, salicyclic, flurbiprofen, sulindac sulphide, sulindac, etodolac, indomethancin, ketorolac tris salt, ketoprofen, mefenamic acid carprofen, baclofen, fenoprofen, and structural analogs thereof.

VI. Anti-Cancer Therapeutics

In another aspect of the invention, the PDZ-binding inhibitory compounds, e.g., COX-2 PDZ-binding inhibitory compounds, identified in accordance with the present invention may be used to treat various cancers, and their therapeutic effectiveness may be increased by optimizing the COX inhibitor structures for binding of the PDZ domains.

COX-2 inhibitors have been known to have anti-oncogenic properties in various cancers. Further, COX-1, COX-2, and PDZ's have been linked to various forms of cancer and tumor growth. The following are some examples and references of work demonstrating the link between COX and various cancers; (a) prostate and colon cancer, M. Hughes-Fulford et. al., "Arachidonic acid, an omega-6 fatty acid, induces cytoplasmic phospholipase A2 in prostate carcinoma cells", *Carcinogenesis*, 2005, 26(9): 1520-6; J.Y. Liou et. al., "Mitochondrial localization of cyclooxygenase-2 and calcium-independent phospholipase A2 in human cancer cells: implication in apoptosis resistance", *Exp. Cell Res.* 2005, 306(1): 75-84; (b) ovarian cancer, T. Daikoku et. al., "Cyclooxygenase-1 is a potential target for prevention and treatment of ovarian epithelial cancer", *Cancer Res.* 2005, 65(9): 3735-44; (c) other cancers may include lung cancer, and cervical cancer (see MAGI1 d1 inhibitor data in the examples, infra).

In accordance with certain aspects of the invention, without being bound by theory, it is believed that the NSAIDS possess anti-oncogenic properties by virtue of their ability to bind PDZ proteins, such as MAGI1 d1, TIP-1, SHANK1, and PSD95. The structures of some COX-2 inhibitors mimic the C-terminal region of PDZ ligands, where a carboxylate group may hydrogen bond with the GLGF loop of PDZ's, and a hydrophobic group may interact with the P0 hydrophobic pocket of PDZ's. As shown in the examples, infra, certain COX-2 inhibitors have been found to have PDZ binding properties, which are believed to have activity in cancer pathology by virtue of their PDZ binding activity in accordance with certain aspects of the invention.

Furthermore, modification of NSAID's for the purpose of increasing their PDZ binding affinity and specificity may generate drugs with higher anti-tumor activity with less undesirable side effects, such as cardiac malfunction and interference anti-coagulation treatment via use of Aspirin. More specifically, COX inhibitors interfere with the binding pocket of aspirin. Aspirin is an anti-coagulant, and interfering with it's effect may lead to coagulation in people depending on aspirin for blood thinning. A downstream complication may be cardiac malfunction. In sum, it has been discovered that COX inhibitors bind to PDZ's, and have "side-effect" related to PDZ binding, as well as others not related to COX-2/PDZ interaction (such as the downstream anti-coagulation effects). Some of these side-effects may be beneficial and may have to do with the underlying activity of these inhibitors themselves.

In certain aspects, the experimental structures of PDZ's (NMR or crystallographic, for example) may be used to aid in the modification and design of COX inhibitors of higher anti-tumor potency and fewer side effects. The following are examples of biological experiments and readouts to determine the anti-tumor efficacy of such the COX inhibitors or optimized COX inhibitors:

Cellular proliferation assays may be used to determine the anti-tumorigenic potency of the COX inhibitors or their optimized variants. A reduction in cellular proliferation of cancer cells by the presence of these compounds may be an indication that the compound has a beneficial therapeutic effect. Such assays are readily described in the literature (Lisa G. Horvath et. al, "Membranous Expression of Secreted Frizzled-Related Protein 4 Predicts for Good Prognosis in Localized Prostate Cancer and Inhibits PC3 Cellular Proliferation in Vitro", *Clinical Cancer Research*, Vol. 10, 621-625, Jan. 15, 2004). In this work, a calorimetric method (Cell Titer 96 kit (Promega) and a manual cell counting approach was used to measure proliferation.

Cellular migration assays may also be used to determine the anti-tumorigenic potency of the COX inhibitors or their optimized variants. A reduction in cellular migration of cancer cells by the presence of these compounds may be an indication that the compound has a beneficial therapeutic effect. Such assays are readily described in the literature (Philippe Merle, et. al, "Functional Consequences of Frizzled-7 Receptor Overexpression in Human Hepatocellular Carcinoma", *Gastroenterology* (Clinical-Liver, Pancreas, and Billiary Tract) 2004; Volume 127, pages 1110-1122). In this example, a luminescence based assay is used to evaluate cell migration and motility. Other migration approaches are described elsewhere.

Colony formation assays may also be used to determine the anti-tumorigenic potency of the COX inhibitors or their optimized variants. A reduction in colony formation of cancer cells by the presence of these compounds may be an indication that the compound has a beneficial therapeutic effect. Such assays are readily described in the literature (Kazutsugu Uematsu et al., "Wnt Pathway Activation in Mesothelioma: Evidence of Dishevelled Overexpression and Transcriptional Activity of β-catenin", *Cancer Research*, volume 63, pages 4547-4551, Aug. 1, 2003). Essentially, cells are grown in soft agar, and colony formation is measured after days to weeks (example: 4 weeks) by staining with a special dye commercially available.

Apoptosis/cell death assays may also be used to determine the anti-tumorigenic potency of the COX inhibitors or their optimized variants. An enhancement of apoptosis/cell death of cancer cells by the presence of these compounds may be an indication that the compound has a beneficial therapeutic effect. Such assays are readily described in the literature (Iwao Mikami et al, "Efficacy of Wnt-1 monoclonal antibody in sarcoma cells", *BMC Cancer*, volume 5:53, pages 1-7, 2005). The method as described in the reference is based on analysis of Annexin V-FITC cell staining by FACS (Fluorescence Activated Cell Sorter, Flow cytometry).

Sensitization towards apoptosis/death by NSAIDs. In this experiment, NSAIDS or NSAID derivatives may be used to sensitize tumor cells to apoptosis or death by chemotherapeutic agents such as cis-platin.

VII. Therapeutic Utility

Compounds identified by the above methods generally find use in modulating PDZ/PL interactions and/or binding between a COX, e.g., COX-1 or COX-2, and a PDZ polypeptide in a cell. Such methods generally involve contacting the cell with a compound or combination of compounds for a time and under conditions sufficient for binding of a PDZ/PL (or multiple PDZ/PLs) to be inhibited. Without being limited by theory, in certain aspects of the invention, as COX-1 and COX-2 have been found to have PDZ ligands, inhibiting the COX-1/PDZ and/or COX-2/PDZ interactions may have additive therapeutic effects.

In yet another aspect, it has been found that certain chiral forms of COX inhibitors do not bind COX enzymatic pockets, but still have observed anti-inflammatory effects. Without being limited by theory, it is believed that the particular chiral form of such COX inhibitors may bind PDZ's and exert their COX activity via their interaction with PDZ's.

The compounds further find use in treating COX-2 mediated conditions, which conditions, as discussed above, include pain, cancer, inflammation and neurological disorders (including damage from acute insult and recovery therefrom). In one embodiment, the subject compounds may be administered to a subject suffering from cancer, pain, and/or inflammation (e.g., arthritis or a similar condition) or, in other embodiments, a subject at risk for or having undergone a stroke or another acute insult-inducing event.

In particular, the subject compounds may be employed to decrease pain and/or inflammation, to decrease side effects of known COX-2 inhibitors, or to improve or repair neuronal circuits within impaired areas of patients with mild to severe traumatic brain injury, including diffuse axonal injury, hypoxic-ischemic encephalopathy and other forms of craniocerebral trauma. Further, the subject compounds may be used to treat infections of the nervous system, such as common bacterial meningitis, and to treat strokes including those caused by ischemic infarction, embolism and haemorrhage such as hypotensive haemorrhage or other causes. Moreover, the compounds may also be useful for the treatment of neurodegenerative diseases including Alzheimer's disease, Lewy Body dementia, Parkinson's disease (PD), Huntington's disease (HD), multiple sclerosis, motor neuron disease, muscular dystrophy, peripheral neuropathies, metabolic disorders of the nervous system including glycogen storage diseases, and other conditions where neurons are damaged or destroyed. In other embodiments, the subject compounds may be used to treat cancer or slow tumor growth. In certain embodiments, the subject compounds may exert their anti-cancer and anti-tumor activity with fewer undesirable side effects, as compared to traditional treatments, such as cardiac malfunction.

In particular embodiments, the subject compound may be co-administered in conjunction with an inhibitor of prostaglandin synthesis by COX-2 (which may be a non-specific or specific COX-2). Such a compound may be a non-steroidal anti-inflammatory drug (NSAID) of a category listed above. In particular embodiments, the compound may be co-administered with, for example, aspirin, indomethacin (Indocin), ibuprofen (Motrin), naproxen (Naprosyn), piroxicam (Feldene), nabumetone (Relafen), rofecoxib (Vioxx), celecoxib (celebrex) or valdecoxib (Bextra). Such COX-2 inhibitors are well known.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

"A Assay" Detection of PDZ-Ligand Binding Using Immobilized PL Peptide

The following describes an assay in which biotinylated candidate PL peptides are immobilized on an avidin-coated surface. The binding of PDZ-domain fusion protein to this surface is then measured. In one embodiment, the PDZ-domain fusion protein is a GST/PDZ fusion protein and the assay is carried out as follows:

(1) Avidin is bound to a surface, e.g., a protein binding surface. In one embodiment, avidin is bound to a polystyrene 96 well plate (e.g., Nunc Polysorb (cat #475094) by addition of 100 μL per well of 20 μg/mL of avidin (Pierce) in phosphate buffered saline without calcium and magnesium, pH 7.4 ("PBS", GibcoBRL) at 4° C. for 12 hours. The plate is then treated to block nonspecific interactions by addition of 200 μL per well of PBS containing 2 g per 100 mL protease-free bovine serum albumin ("PBS/BSA") for 2 hours at 4° C. The plate is then washed 3 times with PBS by repeatedly adding 200 μL per well of PBS to each well of the, plate and then dumping the contents of the plate into a waste container and tapping the plate gently on a dry surface.

(2) Biotinylated PL peptides (or candidate PL peptides) are immobilized on the surface of wells of the plate by addition of 50 uL per well of 0.4 uM peptide in PBS/BSA for 30 minutes at 4° C. Usually, each different peptide is added to at least eight different wells so that multiple measurements (e.g., duplicates and also measurements using different GST/PDZ-domain fusion proteins and a GST alone negative control) can be made, and also additional negative control wells are prepared in which no peptide is immobilized. Following immobilization of the PL peptide on the surface, the plate is washed 3 times with PBS.

(3) GST/PDZ-domain fusion protein (prepared as described supra) is allowed to react with the surface by addition of 50 μL per well of a solution containing 5 μg/mL GST/PDZ-domain fusion protein in PBS/BSA for 2 hours at 4° C. As a negative control, GST alone (i.e., not a fusion protein) is added to specified wells, generally at least 2 wells (i.e., duplicate measurements) for each immobilized peptide. After the 2 hour reaction, the plate is washed 3 times with PBS to remove unbound fusion protein.

(4) The binding of the GST/PDZ-domain fusion protein to the avidin-biotinylated peptide surface can be detected using a variety of methods, and detectors known in the art. In one embodiment, 50 uL per well of an anti-GST antibody in PBS/BSA (e.g., 2.5 μg/mL of polyclonal goat-anti-GST antibody, Pierce) is added to the plate and allowed to react for 20 minutes at 4° C. The plate is washed 3 times with PBS and a second, detectably labeled antibody is added. In one embodiment, 50 μL per well of 2.5 μg/mL of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 μL per well of HRP-substrate solution (TMB, Dako)

for 20 minutes at room temperature (RT). The reaction of the HRP and its substrate is terminated by the addition of 100 μL per well of 1M sulfuric acid and the absorbance (A) of each well of the plate is read at 450 nm.

(5) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g., a T-test) comparing repeated measurements of the signal with repeated measurements of the background will result in a p-value <0.05, more typically a p-value <0.01, and most typically a p-value <0.001 or less.

As noted, in an embodiment of the "A" assay, the signal from binding of a GST/PDZ-domain fusion protein to an avidin surface not exposed to (i.e., not covered with) the PL peptide is one suitable negative control (sometimes referred to as "B"). The signal from binding of GST polypeptide alone (i.e., not a fusion protein) to an avidin-coated surface that has been exposed to (i.e., covered with) the PL peptide is a second suitable negative control (sometimes referred to as "B2"). Because all measurements are done in multiples (i.e., at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2.

Example 2

"G Assay"—Detection of PDZ-Ligand Binding Using Immobilized PDZ-Domain Fusion Polypeptide An assay in which a GST/PDZ fusion protein is immobilized on a surface is described below. ("G" assay). The binding of labeled PL peptide to this surface is then measured. The assay may be carried out as follows:

(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods known to one of skill in the art, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:

(a) 100 μL per well of 5 μg/mL goat anti-GST polyclonal antibody (Pierce) in PBS is added to a polystyrene 96-well plate (e.g., Nunc Polysorb) at 4° C. for 12 hours.

(b) The plate is blocked by addition of 200 μL per well of PBS/BSA for 2 hours at 4° C.

(c) The plate is washed 3 times with PBS.

(d) 50 μL per well of 5 μg/mL GST/PDZ fusion protein or, as a negative control, GST polypeptide alone (i.e., not a fusion protein) in PBS/BSA is added to the plate for 2 hours at 4° C.

(e) The plate is again washed 3 times with PBS (2) Biotinylated PL peptides are allowed to react with the surface by addition of 50 μL per well of 20 μM solution of the biotinylated peptide in PBS/BSA for 10 minutes at 4° C., followed by an additional 20 minute incubation at 25° C. The plate is washed 3 times with ice cold PBS.

(3) The binding of the biotinylated peptide to the GST/PDZ fusion protein surface can be detected using a variety of methods and detectors known to one of skill in the art. In one embodiment, 100 μL per well of 0.5 μg/mL streptavidin-horse radish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 μL per well of HRP-substrate solution (TMB, Dako) for 20 minutes at room temperature (RT). The reaction of the HRP and its substrate is terminated by addition of 100 μL per well of 1M sulfuric acid, and the absorbance of each well of the plate is read at 450 nm.

(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control(s). Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g., a T-test) comparing repeated measurements of the signal with repeated measurements of the background will result in a p-value <0.05, more typically a p-value <0.01, and most typically a p-value <0.001 or less. As noted, in an embodiment of the "G" assay, the signal from binding of a given PL peptide to immobilized (surface bound) GST polypeptide alone is one suitable negative control (sometimes referred to as "B1"). Because all measurement are done in multiples (i.e., at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1.

Example 3

Identification of PDZ Binding Partners of COX-2

Polynucleotides encoding approximately 250 different PDZ domains were cloned into the vector pGEX-3X and expressed according to the methods set forth in U.S. patent application Ser. Nos. 09/710,059, 09/724,553 and 09/688,017. Binding of those PDZ domains was tested against the C-terminus of COX-2 (LLKERSTEL) (SEQ. ID NO. 13) that contains a potential class 1 PDZ-binding domain (PL) conforming to the consensus (S/T-X-V/L) (SEQ. ID. NO. 14). An ELISA-based assay was performed as described below.

Figure 4B:
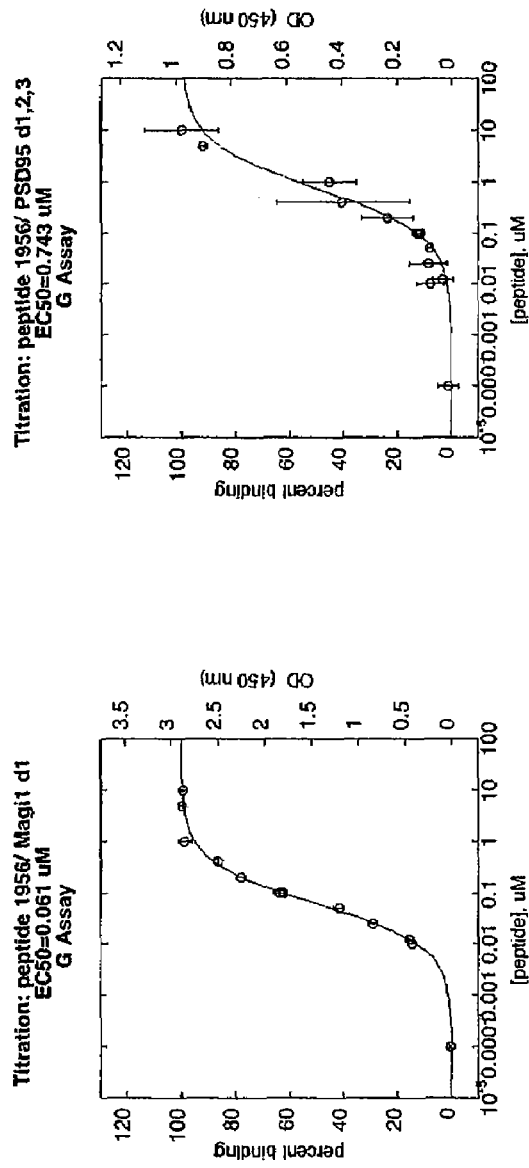
Figure 4C:
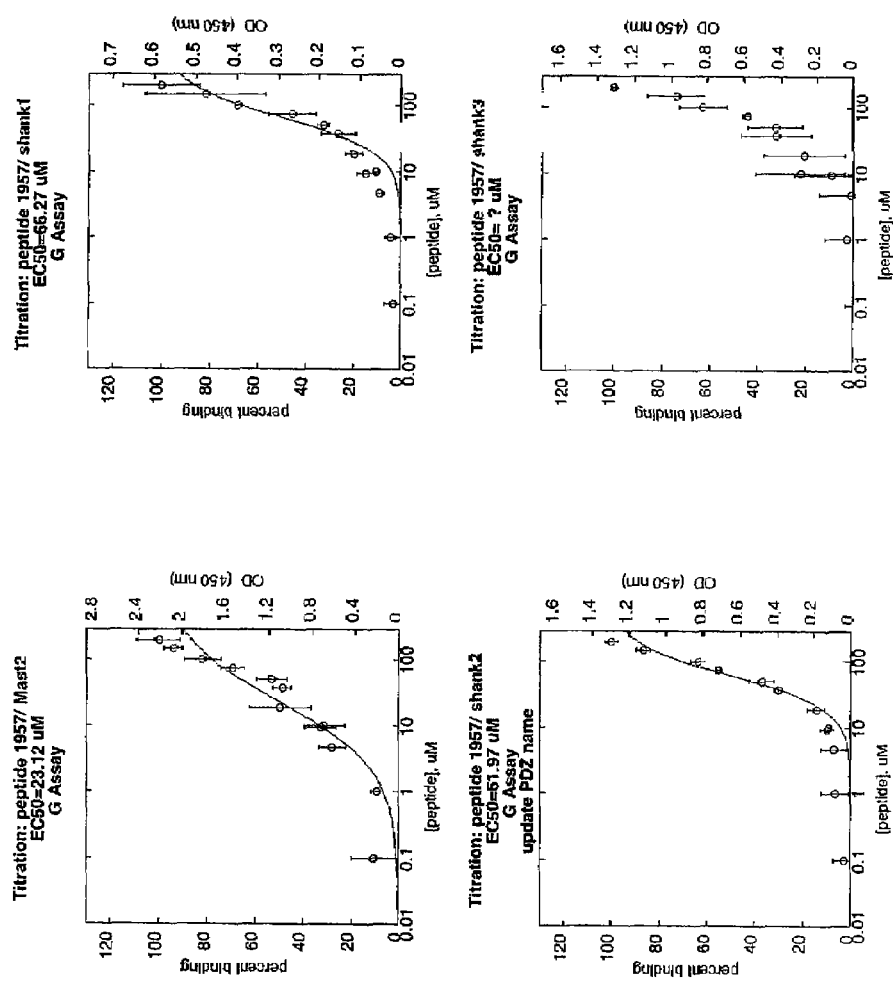

Materials
- Nunc Maxisorp 96 well Immuno-plate (Nunc cat# 62409-005)
- (Maxisorp plates have been shown to have higher background signal)
- PBS pH 7.4 (Gibco BRL cat#16777-148) or
- AVC phosphate buffered saline, 8 gm NaCl, 0.29 gm KCl, 1.44 gm $Na_2HPO_4$, 0.24 gm $KH_2PO_4$, add $H_2O$ to 1 L and pH 7.4; 0.2 micron filter
- 2% BSA/PBS (10 g of bovine serum albumin, fraction V (ICN Biomedicals
- cat# IC15142983) into 500 ml PBS
- Goat anti-GST mAb stock @ 5 mg/ml, store at 4° C., (Amersham Pharmacia
- cat# 27-4577-01), dilute 1:1000 in PBS, final concentration 5 ug/ml
- GST-PDZ fusion protein (stock stored at −80° C. in 35% glycerol, based on pGEX-3X vector), diluted to 5 ug/ml in 2% BSA/PBS
- Peptide: 0.06 uM N-terminally biotinylated Tat-COX-2 peptide in 2% BSA/PBS
- Peptide 1956 sequence: YGRKKRRQRRR<u>LLKERSTEL</u> (SEQ. ID NO. 15) (underlined sequence=wt COX-2 C-terminus, N-terminus is Tat Protein transduction domain sequence for solubility)
- Peptide 1957 sequence: RRRSGLDDINPTV<u>LLKERSTEL</u> (SEQ. ID NO. 92) (underlined sequence=COX-2 C-terminus)
- Wash Buffer, PBS, pH 7.4
- TMB (3,3',5,5', teramethylbensidine), tablets, Sigma cat.#T5525, lot#:
- Per plate, dissolve 1 TMB tablet in 1 mL DMSO, add 9 mL Citrate Phosphate Buffer pH 5.4 and 2 uL $H_2O_2$
- 0.18M $H_2SO_4$ (SIGMA cat.#S1526)
- Hamilton liquid handler, MPH-96
- 250 ml reagent reservoirs,
- 15 ml polypropylene conical tubes
- HRP-Streptavidin, 2.5 mg/2 mL stock, Zymed cat#43-4323
- Dilute 1:2000 in 2% BSA/PBS, Final Concentration 0.5 ug/mL
- Skan Washer 300 version B w/Stacker, Molecular Devices
- Molecular Devices microplate reader (450 nm filters)
- Softmax Pro Software for microplate reader Methods
1. Coat plate with 100 µl of 5 µg/ml anti-GST Ab, O/N @ 4° C.
2. Wash Plate with Plate Washer 3×.
3. Blocking—Add 200 µl per well 2% BSA/PBS
4. Incubate for 2 hrs at RT
5. Rinse off blocking buffer by washing 3 times with 350 µl per well PBS
6. Add 50 µl 5 µg/ml GST-PDZ fusion protein in 2% BSA/PBS (or GST alone as control).
7. Incubate at RT for 2 hours
8. Rinse off excess protein by washing 3 times with 350 ul per well PBS.
9. Add 95 µl of the N-terminally biotinylated peptide
10. Incubate at RT for 30 minutes
11. Rinse off excess peptide by washing 3 times with 350 µl per well PBS.
12. Add 95 µl per well 0.5 µg/ml of HRP-Streptavidin, 20 minutes at RT
13. Rinse by washing 7 times with 350 µl/well with PBS pH 7.4
14. Add 95 µl per well TMB substrate
15. Incubate in dark at room temp, checking plate periodically (5, 10, & 20 minutes)
16. Take early readings, if necessary, at 650 nm
17. At 30 minutes, stop reaction with 95 µl of 0.18M $H_2SO_4$, and take final reading at 450 nm Results The PDZ domains of four proteins SHANK1, SHANK2, SHANK3 and MAST2 were shown to interact with the PL of COX-2. The results are shown in FIG. 3A-3B and FIG. 4A-4C.

Titrations of peptide 1956 involve the Tat transporter peptide sequence (YGRKKRRQRRR, SEQ. ID. NO.: 94) coupled to the wild type 9 C-terminal amino acid sequence of COX-2 (LLKERSTEL, SEQ. ID. NO.: 13) which leads to a higher affinity (lower EC50) towards the various PDZ's relative to peptide 1957, essentially the wild type COX-2 sequence. In accordance with certain embodiments of the invention, binding ehancement affinity of Tat peptide-PDZ ligand/PDZ binding for PDZ ligands may optionally be observed. As such, in certain embodiments, transporter peptides such as Tat may enhance the PDZ binding affinity of PDZ ligands in addition to facilitating the PL peptide entry into the cell.

The sequence of the PDZ domains of SHANK1, SHANK2, SHANK3 and MAST2 employed in these assays are set forth below:

```
SHANK1 (GID 7025450):
ILKEKTVLLQKKDSEGFGFVLRGAKAQTPIEEFT    (SEQ. ID NO. 16)
PTPAFPALQYLESVDEGGVAWRAGLRMGDFLIEV
NGQNVVKVGHRQVVNMIRQGGNTLMVKVVMVTRH
PDMDEAVQNSS

SHANK2 (GID 6049185):
ILEEKTVVLQKKDNEGFGFVLRGAKADTPIEEFT    (SEQ. ID NO. 17)
PTPAFPALQYLESVDEGGVAWQAGLRTGDFLIEV
NNENVVKVGHRQVVNMIRQGGNHLVLKVVTVTRN
LDPDDNSS

SHANK3 (XM_037493 GID: 51476100):
SDYVIDDKVAVLQKRDHEGFGFVLRGAKAETPIE    (SEQ. ID NO. 18)
EFTPTPAFPALQYLESVDVEGVAWRAGLRTGDFL
IEVNGVNVVKVGHKQVVALIRQGGNRLVMKVVSV
TRKPEEDG

MAST2 (Accession no. AB047005):
ISALGSMRPPIIIHRAGKKYGFTLRAIRVYMGDS    (SEQ. ID. NO. 19)
DVYTVHHMVWHVEDGGPASEAGLRQGDLITHVNG
EPVHGLVHTEVVELILKSGNKVAISTTPLENSS
```

In a further experiment, the PDZ domains of SHANK1, SHANK2, SHANK3 and MAST2 were used to identify further PDZ domains (other than that of COX-2) that bind to SHANK1, SHANK2, SHANK3 and MAST2. A list of PDZ ligands that bind to SHANK1, SHANK2 or SHANK3 is set forth in FIG. 5A. A list of PDZ ligands that bind to MAST2 is set forth in FIG. 5B.

Such polypeptides and their variants and analogs may also be employed to inhibit binding between COX-2 and SHANK1, SHANK2, SHANK3 and MAST2 in a cell.

The above results and discussion demonstrate new COX-2 interacting proteins. Knowledge of the interaction provides a means for identifying drugs that can modulate the COX-2. Accordingly, the subject methods represent a significant contribution to the art.

Example 4

Drug Competition Assay—Matrix ELISA Modified G Assay

The assay described in this example may be used in accordance with certain embodiments of the invention to determine the efficacy of candidate inhibitory compounds in disrupting PDZ/PL binding or PDZ/COX-2 binding. The complete protocol and list of reagents/supplies is provided below.

Materials:
1) Nunc Maxisorp 96 well Immuno-plates
2) PBS pH 7.4 (phosphate buffered saline, 8 g NaCl, 0.29 g KCl, 1.44 g $Na_2HPO_4$, 0.24 g
3) $KH_2PO_4$, add $H_2O$ to 1 L and pH 7.4; 0.2µ filter)
4) Assay Buffer: 2% BSA in PBS (20 g of BSA per liter PBS), ICN Biomedicals
5) Goat anti-GST polyclonal antibody, stock 5 mg/ml, stored at 4° C., Amersham Pharmacia
6) Dilute 1:1000 in PBS, final concentration 5 µg/ml
7) HRP-Streptavidin, 2.5 mg/2 ml stock stored @ 4° C., Zymed,
   dilute 1:2000 into Assay buffer, final [0.5 µg/ml]
8) Biotinylated peptides (from Anaspec, stored in −20° C. freezer)
9) GST-PRISM proteins (stock stored @ −80° C., after $1^{st}$ thaw store in −10° C. freezer)
10) TMB (3,3',5,5', teramethylbensidine), ready to use
11) 0.18M $H_2SO_4$
12) 12-w multichannel pipettor
13) 200 µL LTS tips
14) 50 ml reagent reservoirs
15) 50 polypropylene conical tubes
16) 15 mL polypropylene round-bottom tubes
17) 1.5 mL microtubes
18) Costar Transtar 96
19) Transtar 96 Cartridge
20) Molecular Devices microplate reader (450 nm filters)
21) SoftMax Pro software
22) Assay buffer (1×PBS, 0.01% Triton X-100)

Methods:
18-20 plates were coated with 100 µl of 5 µg/ml anti-GST antibody in each well, and left overnight at 4° C. The plates were then emptied by inverting and tapped dry on paper towels. 200 µl of blocking buffer (1×PBS/2% BSA) was added to each well and the plates were left for 1-2 hrs at room temperature. The proteins were then diluted to the required concentration in 1×PBS/2% BSA. The plates were then washed using the automatic plate washer (3× with room temperature 1×PBS), ensuring that the plates did not dry out. Proteins were added to the wells at 50 µl per well and were incubated for 1-2 hours at 4° C.

The peptides, drugs, and HRP were then prepared in Assay Buffer as follows:

Peptides were prepared in one-quarter final volume at 4× final concentration.

HRP was diluted (1:500) in one-quarter final volume at 4× final concentration.

Peptides and HRP were then mixed together, and incubated for 20 minutes at room temperature.

Whilst the peptide/HRP mix was incubating, the drug titrations were prepared in half the final volume at 2× final concentration.

Immediately before adding the final mixture to the plate, the drug titration was combined with the peptide-HRP solution (mixture should now be correct total volume and final concentrations).

The following PDZ peptide/PL combinations were tested with the following drugs (alternatively, a COX-2 PL sequence may be used). Exemplary PDZ domain sequences are illustrated in FIG. 6.

| PDZ | PL Sequence |
|---|---|
| MAGI1 d1 (AVC 88) | GRWTGRSMSSWKPTRRETEV (AVC 1857) (SEQ. ID NO. 20) |
| TIP-1 (AVC 54) | QISPGGLEPPSEKHFRETEV (AVC AA56) (SEQ. ID NO. 21) |
| SHANK1 (AVC 235) | YGRKKRRQRRRYIPEAQTRL (AVC 1965) (SEQ. ID NO. 22) |
| PSD95 d1 (AVC 143) | YGRKKRRQRRRRISSIETDV (AVC 1912) (SEQ. ID NO. 23) |
| PSD95 d2 (AVC 265) | YGRKKRRQRRRKLSSIESDV (AVC AA348) (SEQ. ID NO. 24) |
| PSD95 d3 (AVC 466) | YGRKKRRQRRRTKNYKQTSV (AVC 1916) (SEQ. ID NO. 25) |

Drugs tested: 1) Niflumic acid; 2) Ibuprofen; 3) Naproxen sodium; 4) Diclofenac sodium salt; 5) Acetylsalicylic acid; 6) Salicylic; 7) Flurbiprofen; 8) Sulindac sulphide; 9) Sulindac; 10) Etodolac; 11) Indomethacin; 12) Ketorolac Tris salt; 13) Ketoprofen; 14) Mefenamic acid; 15) Carprofen; 16) Baclofen; 17) Fenoprofen; 18) Benztropine mesylate; 19) Amitriptyline HCl; 20) Cromolyn sodium; 21) Desipramine HCl; 22) Clomipramine HCl; 23) Nortriptyline HCl, as recognized by those skilled in the art, (1-17 are COX-2 inhibitors).

The plates were then washed using the automatic plate washer (3× with room temperature 1×PBS). The peptide/HRP/drug mixtures were then added to the plates at 50 µl per well and the time of addition of the mixture was recorded on each plate. The plates were then incubated at room temperature, after the last peptide had been added, for exactly 30 minutes.

The plate reader was turned on the computer files were prepared during the incubation. The plates were then washed using the automatic plate washer (7× with room temperature 1×PBS). TMB substrate was then added to the plates at 100 µl per well and the time of TMB addition was written on each plate. The plates were then incubated in the dark at room temperature for a maximum of 30 minutes. The reaction was then stopped using 100 µl of 0.18M $H_2SO_4$ 30 minutes after adding TMB. The plates were then read at 450 nm immediately after stopping the reaction.

Results:
Results are shown in FIGS. 7A-7G, where the drugs were competing with biotinylated peptides for binding to the PDZ capture proteins on the ELISA plate. A decrease in the base OD signal (for the peptide-PDZ interaction) corresponds to an increase in drug-PDZ binding and successful competition of the drug against the biotinylated peptide.

All publications and patents cited in this specification are herein incorporated by reference as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An assay for detecting an inhibitor of binding between cyclooxygenase-2 (COX-2) and a PDZ protein, comprising:
contacting a PDZ-containing polypeptide with a COX-2 PDZ ligand-containing polypeptide in the presence and absence of a test agent, and
determining binding between the PDZ-containing polypeptide with a COX-2 PDZ ligand-containing polypeptide in the presence and absence of the test agent;
wherein reduced binding in the presence of the test agent indicates that the test agent inhibits binding of a PDZ-containing polypeptide to a COX-2 PDZ ligand-containing polypeptide, and wherein the COX-2 PDZ ligand-containing polypeptide comprises at least five contiguous C-terminal amino acids from SEQ ID NO: 13.

2. The assay of claim 1, wherein said PDZ-containing polypeptide contains a PDZ domain of MAGI1, TIP-1, MAST2, PSD95, or SHANK.

3. The assay of claim 2, wherein said PDZ-containing polypeptide comprises a PDZ domain of SHANK1, SHANK2 or SHANK-3.

4. The assay of claim 2, wherein said PDZ-containing polypeptide comprises a PDZ domain of MAGI1.

5. The assay of claim 2, wherein said PDZ-containing polypeptide comprises a PDZ domain of PSD95.

6. The assay of claim 1, wherein said assay is a cell-free assay.

7. The assay of claim 1, wherein said assay is a cellular assay.

8. The assay of claim 7, wherein said assay is a two hybrid assay.

9. The assay of claim 7, wherein said assay is a FRET-based assay.

10. The assay of claim 7, wherein said assay is performed using neuronal cells that contain said PDZ domain-containing polypeptide and said COX-2 PDZ ligand-containing polypeptide.

11. The assay of claim 1, wherein said assay further comprises testing said agent for COX-2 cyclooxygenase inhibitory activity.

12. The assay of claim 1, wherein said test agent is a known inhibitor of a cyclooxygenase activity of COX-2.

13. The assay of claim 1, wherein said test agent comprises a PDZ domain analog.

14. The assay of claim 1, further comprising testing said compound in a neuronal cell.

15. The assay of claim 14, further comprising subjecting said neuronal cell to insult.

16. The assay of claim 15, wherein said insult is hypoxia or ischemia.

17. The method of claim 1, wherein if the test agent is found to inhibit said binding, the method further comprises determining whether the test agent has anti-tumor and/or anti-cellular proliferation properties when administered in vivo.

18. The method of claim 17, wherein the test agent is tested for anti-tumor and/or anti-cellular proliferation properties in vitro.

19. The method of claim 1, comprising
contacting multiple PDZ-containing polypeptides with a COX-2 PDZ ligand-containing polypeptide in the presence and absence of a test agent, and
determining specific binding between each of the multiple PDZ-containing polypeptides with a COX-2 PDZ ligand-containing polypeptide in the presence and absence of the test agent.

20. The method of claim 19, wherein the ability of the target agent to selectively inhibit binding of a particular PDZ-containing polypeptides with the COX-2 PDZ ligand-containing polypeptide is determined.

21. The method of claim 20, wherein the ability of multiple test agents to selectively inhibit said binding is determined.

22. The method of claim 1, wherein the ability of multiple test agents to inhibit said binding is determined.

* * * * *

SEQUENCE LISTING

```
<160> NUMBER OF SEQ ID NOS: 94

<210> SEQ ID NO 1
<211> LENGTH: 89
<212> TYPE: PRT
<213> ORGANISM: Homo sapiens

<400> SEQUENCE: 1

Val Leu Leu Gln Lys Lys Asp Ser Glu Gly Phe Gly Phe Val Leu Arg
 1               5                  10                  15

Gly Ala Lys Ala Gln Thr Pro Ile Glu Glu Phe Thr Pro Thr Pro Ala
            20                  25                  30

Phe Pro Ala Leu Gln Tyr Leu Glu Ser Val Asp Glu Gly Gly Val Ala
        35                  40                  45

Trp Arg Ala Gly Leu Arg Met Gly Asp Phe Leu Ile Glu Val Asn Gly
    50                  55                  60

Gln Asn Val Val Lys Val Gly His Arg Gln Val Val Asn Met Ile Arg
65                  70                  75                  80

Gln Gly Gly Asn Thr Leu Met Val Lys
                85

<210> SEQ ID NO 2
<211> LENGTH: 109
<212> TYPE: PRT
<213> ORGANISM: Homo sapiens

<400> SEQUENCE: 2

Gly Ser Asp Tyr Ile Ile Lys Glu Lys Thr Val Leu Leu Gln Lys Lys
 1               5                  10                  15

Asp Ser Glu Gly Phe Gly Phe Val Leu Arg Gly Ala Lys Ala Gln Thr
            20                  25                  30

Pro Ile Glu Glu Phe Thr Pro Thr Pro Ala Phe Pro Ala Leu Gln Tyr
        35                  40                  45

Leu Glu Ser Val Asp Glu Gly Gly Val Ala Trp Arg Ala Gly Leu Arg
    50                  55                  60

Met Gly Asp Phe Leu Ile Glu Val Asn Gly Gln Asn Val Val Lys Val
65                  70                  75                  80

Gly His Arg Gln Val Val Asn Met Ile Arg Gln Gly Gly Asn Thr Leu
                85                  90                  95

Met Val Lys Val Val Met Val Thr Arg His Pro Asp Met
            100                 105

<210> SEQ ID NO 3
<211> LENGTH: 129
```

```
<212> TYPE: PRT
<213> ORGANISM: Homo sapiens

<400> SEQUENCE: 3

Ala Pro Ser Leu Met Asp Gly Ile Gly Pro Gly Ser Asp Tyr Ile Ile
 1               5                  10                  15

Lys Glu Lys Thr Val Leu Leu Gln Lys Lys Asp Ser Glu Gly Phe Gly
                20                  25                  30

Phe Val Leu Arg Gly Ala Lys Ala Gln Thr Pro Ile Glu Glu Phe Thr
            35                  40                  45

Pro Thr Pro Ala Phe Pro Ala Leu Gln Tyr Leu Glu Ser Val Asp Glu
        50                  55                  60

Gly Gly Val Ala Trp Arg Ala Gly Leu Arg Met Gly Asp Phe Leu Ile
65                  70                  75                  80

Glu Val Asn Gly Gln Asn Val Val Lys Val Gly His Arg Gln Val Val
                85                  90                  95

Asn Met Ile Arg Gln Gly Gly Asn Thr Leu Met Val Lys Val Val Met
            100                 105                 110

Val Thr Arg His Pro Asp Met Asp Glu Ala Val His Lys Lys Ala Pro
        115                 120                 125

Gly

<210> SEQ ID NO 4
<211> LENGTH: 89
<212> TYPE: PRT
<213> ORGANISM: Homo sapiens

<400> SEQUENCE: 4

Val Val Leu Gln Lys Lys Asp Asn Glu Gly Phe Gly Phe Val Leu Arg
 1               5                  10                  15

Gly Ala Lys Ala Asp Thr Pro Ile Glu Glu Phe Thr Pro Thr Pro Ala
                20                  25                  30

Phe Pro Ala Leu Gln Tyr Leu Glu Ser Val Asp Glu Gly Gly Val Ala
            35                  40                  45

Trp Gln Ala Gly Leu Arg Thr Gly Asp Phe Leu Ile Glu Val Asn Asn
        50                  55                  60

Glu Asn Val Val Lys Val Gly His Arg Gln Val Val Asn Met Ile Arg
65                  70                  75                  80

Gln Gly Gly Asn His Leu Val Leu Lys
                85

<210> SEQ ID NO 5
<211> LENGTH: 109
<212> TYPE: PRT
<213> ORGANISM: Homo sapiens

<400> SEQUENCE: 5

Tyr Ser Asp Cys Ile Ile Glu Glu Lys Thr Val Val Leu Gln Lys Lys
 1               5                  10                  15

Asp Asn Glu Gly Phe Gly Phe Val Leu Arg Gly Ala Lys Ala Asp Thr
                20                  25                  30

Pro Ile Glu Glu Phe Thr Pro Thr Pro Ala Phe Pro Ala Leu Gln Tyr
            35                  40                  45

Leu Glu Ser Val Asp Glu Gly Gly Val Ala Trp Gln Ala Gly Leu Arg
        50                  55                  60

Thr Gly Asp Phe Leu Ile Glu Val Asn Asn Glu Asn Val Val Lys Val
65                  70                  75                  80
```

```
Gly His Arg Gln Val Val Asn Met Ile Arg Gln Gly Gly Asn His Leu
                85                  90                  95

Val Leu Lys Val Val Thr Val Thr Arg Asn Leu Asp Pro
            100                 105

<210> SEQ ID NO 6
<211> LENGTH: 129
<212> TYPE: PRT
<213> ORGANISM: Homo sapiens

<400> SEQUENCE: 6

Asn Asn Gly Arg Cys Pro Arg Asn Ser Leu Tyr Ser Asp Cys Ile Ile
1               5                   10                  15

Glu Glu Lys Thr Val Val Leu Gln Lys Lys Asp Asn Glu Gly Phe Gly
            20                  25                  30

Phe Val Leu Arg Gly Ala Lys Ala Asp Thr Pro Ile Glu Glu Phe Thr
        35                  40                  45

Pro Thr Pro Ala Phe Pro Ala Leu Gln Tyr Leu Glu Ser Val Asp Glu
    50                  55                  60

Gly Gly Val Ala Trp Gln Ala Gly Leu Arg Thr Gly Asp Phe Leu Ile
65                  70                  75                  80

Glu Val Asn Asn Glu Asn Val Val Lys Val Gly His Arg Gln Val Val
                85                  90                  95

Asn Met Ile Arg Gln Gly Gly Asn His Leu Val Leu Lys Val Val Thr
            100                 105                 110

Val Thr Arg Asn Leu Asp Pro Asp Thr Ala Arg Lys Lys Ala Pro
        115                 120                 125

Pro

<210> SEQ ID NO 7
<211> LENGTH: 89
<212> TYPE: PRT
<213> ORGANISM: Homo sapiens

<400> SEQUENCE: 7

Ala Val Leu Gln Lys Arg Asp His Glu Gly Phe Gly Phe Val Leu Arg
1               5                   10                  15

Gly Ala Lys Ala Glu Thr Pro Ile Glu Glu Phe Thr Pro Thr Pro Ala
            20                  25                  30

Phe Pro Ala Leu Gln Tyr Leu Glu Ser Val Asp Val Glu Gly Val Ala
        35                  40                  45

Trp Arg Ala Gly Leu Arg Thr Gly Asp Phe Leu Ile Glu Val Asn Gly
    50                  55                  60

Val Asn Val Val Lys Val Gly His Lys Gln Val Val Ala Leu Ile Arg
65                  70                  75                  80

Gln Gly Gly Asn Arg Leu Val Met Lys
                85

<210> SEQ ID NO 8
<211> LENGTH: 109
<212> TYPE: PRT
<213> ORGANISM: Homo sapiens

<400> SEQUENCE: 8

His Ser Asp Tyr Val Ile Asp Asp Lys Val Ala Val Leu Gln Lys Arg
1               5                   10                  15

Asp His Glu Gly Phe Gly Phe Val Leu Arg Gly Ala Lys Ala Glu Thr
```

-continued

```
                    20                  25                  30
Pro Ile Glu Glu Phe Thr Pro Thr Pro Ala Phe Pro Ala Leu Gln Tyr
            35                  40                  45

Leu Glu Ser Val Asp Val Glu Gly Val Ala Trp Arg Ala Gly Leu Arg
    50                  55                  60

Thr Gly Asp Phe Leu Ile Glu Val Asn Gly Val Asn Val Val Lys Val
65                  70                  75                  80

Gly His Lys Gln Val Val Ala Leu Ile Arg Gln Gly Gly Asn Arg Leu
                85                  90                  95

Val Met Lys Val Val Ser Val Thr Arg Lys Pro Glu Glu
            100                 105
```

<210> SEQ ID NO 9
<211> LENGTH: 129
<212> TYPE: PRT
<213> ORGANISM: Homo sapiens

<400> SEQUENCE: 9

```
Thr Val Gly Ser Tyr Asp Ser Leu Thr Ser His Ser Asp Tyr Val Ile
1               5                   10                  15

Asp Asp Lys Val Ala Val Leu Gln Lys Arg Asp His Glu Gly Phe Gly
                20                  25                  30

Phe Val Leu Arg Gly Ala Lys Ala Glu Thr Pro Ile Glu Glu Phe Thr
            35                  40                  45

Pro Thr Pro Ala Phe Pro Ala Leu Gln Tyr Leu Glu Ser Val Asp Val
        50                  55                  60

Glu Gly Val Ala Trp Arg Ala Gly Leu Arg Thr Gly Asp Phe Leu Ile
65                  70                  75                  80

Glu Val Asn Gly Val Asn Val Val Lys Val Gly His Lys Gln Val Val
                85                  90                  95

Ala Leu Ile Arg Gln Gly Gly Asn Arg Leu Val Met Lys Val Val Ser
            100                 105                 110

Val Thr Arg Lys Pro Glu Glu Asp Gly Ala Arg Arg Ala Met Lys
        115                 120                 125

Lys
```

<210> SEQ ID NO 10
<211> LENGTH: 79
<212> TYPE: PRT
<213> ORGANISM: Homo sapiens

<400> SEQUENCE: 10

```
Ile His Arg Ala Gly Lys Lys Tyr Gly Phe Thr Leu Arg Ala Ile Arg
1               5                   10                  15

Val Tyr Met Gly Asp Ser Asp Val Tyr Thr Val His His Met Val Trp
                20                  25                  30

His Val Glu Asp Gly Gly Pro Ala Ser Glu Ala Gly Leu Arg Gln Gly
            35                  40                  45

Asp Leu Ile Thr His Val Asn Gly Glu Pro Val His Gly Leu Val His
        50                  55                  60

Thr Glu Val Val Glu Leu Ile Leu Lys Ser Gly Asn Lys Val Ala
65                  70                  75
```

<210> SEQ ID NO 11
<211> LENGTH: 99
<212> TYPE: PRT
<213> ORGANISM: Homo sapiens

<400> SEQUENCE: 11

Ala Leu Gly Ser Met Arg Pro Ile Ile Ile His Arg Ala Gly Lys
1               5                   10                  15

Lys Tyr Gly Phe Thr Leu Arg Ala Ile Arg Val Tyr Met Gly Asp Ser
                20                  25                  30

Asp Val Tyr Thr Val His His Met Val Trp His Val Glu Asp Gly Gly
            35                  40                  45

Pro Ala Ser Glu Ala Gly Leu Arg Gln Gly Asp Leu Ile Thr His Val
        50                  55                  60

Asn Gly Glu Pro Val His Gly Leu Val His Thr Glu Val Val Glu Leu
65                  70                  75                  80

Ile Leu Lys Ser Gly Asn Lys Val Ala Ile Ser Thr Thr Pro Leu Glu
                85                  90                  95

Asn Thr Ser

<210> SEQ ID NO 12
<211> LENGTH: 119
<212> TYPE: PRT
<213> ORGANISM: Homo sapiens

<400> SEQUENCE: 12

Asp Ser Ser Pro Ser Arg Asp Phe Leu Pro Ala Leu Gly Ser Met Arg
1               5                   10                  15

Pro Pro Ile Ile Ile His Arg Ala Gly Lys Lys Tyr Gly Phe Thr Leu
                20                  25                  30

Arg Ala Ile Arg Val Tyr Met Gly Asp Ser Asp Val Tyr Thr Val His
            35                  40                  45

His Met Val Trp His Val Glu Asp Gly Gly Pro Ala Ser Glu Ala Gly
        50                  55                  60

Leu Arg Gln Gly Asp Leu Ile Thr His Val Asn Gly Glu Pro Val His
65                  70                  75                  80

Gly Leu Val His Thr Glu Val Val Glu Leu Ile Leu Lys Ser Gly Asn
                85                  90                  95

Lys Val Ala Ile Ser Thr Thr Pro Leu Glu Asn Thr Ser Ile Lys Val
                100                 105                 110

Gly Pro Ala Arg Lys Gly Ser
        115

<210> SEQ ID NO 13
<211> LENGTH: 9
<212> TYPE: PRT
<213> ORGANISM: Homo sapiens

<400> SEQUENCE: 13

Leu Leu Lys Glu Arg Ser Thr Glu Leu
1               5

<210> SEQ ID NO 14
<211> LENGTH: 3
<212> TYPE: PRT
<213> ORGANISM: Homo sapiens
<220> FEATURE:
<221> NAME/KEY: MOD_RES
<222> LOCATION: (1)
<223> OTHER INFORMATION: Ser or Thr
<220> FEATURE:
<221> NAME/KEY: MOD_RES
<222> LOCATION: (2)
<223> OTHER INFORMATION: variable amino acid

```
<220> FEATURE:
<221> NAME/KEY: MOD_RES
<222> LOCATION: (3)
<223> OTHER INFORMATION: Val or Leu

<400> SEQUENCE: 14

Xaa Xaa Xaa
  1

<210> SEQ ID NO 15
<211> LENGTH: 20
<212> TYPE: PRT
<213> ORGANISM: Homo sapiens

<400> SEQUENCE: 15

Tyr Gly Arg Lys Lys Arg Arg Gln Arg Arg Leu Leu Lys Glu Arg
  1               5                  10                  15

Ser Thr Glu Leu
            20

<210> SEQ ID NO 16
<211> LENGTH: 113
<212> TYPE: PRT
<213> ORGANISM: Homo sapiens

<400> SEQUENCE: 16

Ile Leu Lys Glu Lys Thr Val Leu Leu Gln Lys Lys Asp Ser Glu Gly
  1               5                  10                  15

Phe Gly Phe Val Leu Arg Gly Ala Lys Ala Gln Thr Pro Ile Glu Glu
                 20                  25                  30

Phe Thr Pro Thr Pro Ala Phe Pro Ala Leu Gln Tyr Leu Glu Ser Val
             35                  40                  45

Asp Glu Gly Gly Val Ala Trp Arg Ala Gly Leu Arg Met Gly Asp Phe
         50                  55                  60

Leu Ile Glu Val Asn Gly Gln Asn Val Val Lys Val Gly His Arg Gln
 65                  70                  75                  80

Val Val Asn Met Ile Arg Gln Gly Gly Asn Thr Leu Met Val Lys Val
                 85                  90                  95

Val Met Val Thr Arg His Pro Asp Met Asp Glu Ala Val Gln Asn Ser
                100                 105                 110

Ser

<210> SEQ ID NO 17
<211> LENGTH: 110
<212> TYPE: PRT
<213> ORGANISM: Homo sapiens

<400> SEQUENCE: 17

Ile Leu Glu Glu Lys Thr Val Val Leu Gln Lys Lys Asp Asn Glu Gly
  1               5                  10                  15

Phe Gly Phe Val Leu Arg Gly Ala Lys Ala Asp Thr Pro Ile Glu Glu
                 20                  25                  30

Phe Thr Pro Thr Pro Ala Phe Pro Ala Leu Gln Tyr Leu Glu Ser Val
             35                  40                  45

Asp Glu Gly Gly Val Ala Trp Gln Ala Gly Leu Arg Thr Gly Asp Phe
         50                  55                  60

Leu Ile Glu Val Asn Asn Glu Asn Val Val Lys Val Gly His Arg Gln
 65                  70                  75                  80

Val Val Asn Met Ile Arg Gln Gly Gly Asn His Leu Val Leu Lys Val
```

```
                85                  90                  95
Val Thr Val Thr Arg Asn Leu Asp Pro Asp Asp Asn Ser Ser
            100                 105                 110

<210> SEQ ID NO 18
<211> LENGTH: 110
<212> TYPE: PRT
<213> ORGANISM: Homo sapiens

<400> SEQUENCE: 18

Ser Asp Tyr Val Ile Asp Lys Val Ala Val Leu Gln Lys Arg Asp
 1               5                  10                  15

His Glu Gly Phe Gly Phe Val Leu Arg Gly Ala Lys Ala Glu Thr Pro
                20                  25                  30

Ile Glu Glu Phe Thr Pro Thr Pro Ala Phe Pro Ala Leu Gln Tyr Leu
            35                  40                  45

Glu Ser Val Asp Val Glu Gly Val Ala Trp Arg Ala Gly Leu Arg Thr
        50                  55                  60

Gly Asp Phe Leu Ile Glu Val Asn Gly Val Asn Val Val Lys Val Gly
 65                 70                  75                  80

His Lys Gln Val Val Ala Leu Ile Arg Gln Gly Gly Asn Arg Leu Val
                85                  90                  95

Met Lys Val Ser Val Thr Arg Lys Pro Glu Glu Asp Gly
            100                 105                 110

<210> SEQ ID NO 19
<211> LENGTH: 101
<212> TYPE: PRT
<213> ORGANISM: Homo sapiens

<400> SEQUENCE: 19

Ile Ser Ala Leu Gly Ser Met Arg Pro Ile Ile His Arg Ala
 1               5                  10                  15

Gly Lys Lys Tyr Gly Phe Thr Leu Arg Ala Ile Arg Val Tyr Met Gly
                20                  25                  30

Asp Ser Asp Val Tyr Thr Val His His Met Val Trp His Val Glu Asp
            35                  40                  45

Gly Gly Pro Ala Ser Glu Ala Gly Leu Arg Gln Gly Asp Leu Ile Thr
        50                  55                  60

His Val Asn Gly Glu Pro Val His Gly Leu Val His Thr Glu Val Val
 65                 70                  75                  80

Glu Leu Ile Leu Lys Ser Gly Asn Lys Val Ala Ile Ser Thr Thr Pro
                85                  90                  95

Leu Glu Asn Ser Ser
            100

<210> SEQ ID NO 20
<211> LENGTH: 20
<212> TYPE: PRT
<213> ORGANISM: Homo sapiens

<400> SEQUENCE: 20

Gly Arg Trp Thr Gly Arg Ser Met Ser Ser Trp Lys Pro Thr Arg Arg
 1               5                  10                  15

Glu Thr Glu Val
            20

<210> SEQ ID NO 21
```

```
<211> LENGTH: 20
<212> TYPE: PRT
<213> ORGANISM: Homo sapiens

<400> SEQUENCE: 21

Gln Ile Ser Pro Gly Gly Leu Glu Pro Pro Ser Glu Lys His Phe Arg
 1               5                  10                  15

Glu Thr Glu Val
            20

<210> SEQ ID NO 22
<211> LENGTH: 20
<212> TYPE: PRT
<213> ORGANISM: Homo sapiens

<400> SEQUENCE: 22

Tyr Gly Arg Lys Lys Arg Arg Gln Arg Arg Arg Tyr Ile Pro Glu Ala
 1               5                  10                  15

Gln Thr Arg Leu
            20

<210> SEQ ID NO 23
<211> LENGTH: 20
<212> TYPE: PRT
<213> ORGANISM: Homo sapiens

<400> SEQUENCE: 23

Tyr Gly Arg Lys Lys Arg Arg Gln Arg Arg Arg Ile Ser Ser Ile
 1               5                  10                  15

Glu Thr Asp Val
            20

<210> SEQ ID NO 24
<211> LENGTH: 20
<212> TYPE: PRT
<213> ORGANISM: Homo sapiens

<400> SEQUENCE: 24

Tyr Gly Arg Lys Lys Arg Arg Gln Arg Arg Arg Lys Leu Ser Ser Ile
 1               5                  10                  15

Glu Ser Asp Val
            20

<210> SEQ ID NO 25
<211> LENGTH: 20
<212> TYPE: PRT
<213> ORGANISM: Homo sapiens

<400> SEQUENCE: 25

Tyr Gly Arg Lys Lys Arg Arg Gln Arg Arg Arg Thr Lys Asn Tyr Lys
 1               5                  10                  15

Gln Thr Ser Val
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

-continued

```
Pro Ile Pro Ala Gly Gly Cys Thr Phe Ser Gly Ile Phe Pro Thr Leu
1               5                   10                  15

Thr Ser Pro Leu
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Gln Phe His Arg Gly Ser Arg Ala Gln Ser Phe Leu Gln Thr Glu
1               5                   10                  15

Thr Ser Val Ile
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Arg Glu Asp Ile Tyr Val Asn Tyr Pro Thr Phe Ser Arg Arg Pro
1               5                   10                  15

Lys Thr Arg Val
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Glu Asn Asp Tyr Glu Ser Ile Ser Asp Leu Gln Gln Gly Arg Asp
1               5                   10                  15

Ile Thr Arg Leu
            20

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Trp Asp Asp Ser Ala Arg Ala Ala Gly Gly Gln Gly Leu His Val
1               5                   10                  15

Thr Ala Leu

<210> SEQ ID NO 31
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 31

Lys Asp Ser Arg Pro Ser Phe Val Gly Ser Ser Ser Gly His Thr Ser
 1               5                  10                  15

Thr Thr Leu

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Pro Gln Ile Ala Ala Leu Lys Glu Glu Thr Glu Glu Glu Val Gln
 1               5                  10                  15

Asp Thr Arg Leu
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Ser Trp Arg Arg Ser Ser Leu Ser Glu Ser Glu Asn Ala Thr Ser
 1               5                  10                  15

Leu Thr Thr Phe
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Gly Gly Arg Ser Ala Arg Gly Gly Arg Leu Gln Gly Arg Arg
 1               5                  10                  15

Glu Thr Ala Leu
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Pro Ala Thr Pro Ser Pro Arg Leu Ala Leu Pro Ala His His Asn
 1               5                  10                  15

Ala Thr Arg Leu
            20
```

```
<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Ala Ala Gly Phe Asn Ser Thr Gly Leu Pro His Ser Thr Thr
 1               5                  10                  15

Arg Val

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Ser Asp Pro Glu Asn Glu Pro Phe Asp Glu Asp Gln His Thr Gln
 1               5                  10                  15

Ile Thr Lys Val
         20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Asp Phe Arg Arg Ala Phe Arg Arg Ile Leu Ala Arg Pro Trp Thr
 1               5                  10                  15

Gln Thr Ala Trp
         20

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Ser Lys Ser Lys Ser Ser Glu Glu Ser Gln Thr Phe Phe Gly Leu
 1               5                  10                  15

Tyr Lys Leu

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Ala Leu Gln Pro Glu Pro Gly Arg Lys Arg Ile Pro Leu Thr Arg
 1               5                  10                  15
```

-continued

```
Thr Thr Thr Phe
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Ala Ser Lys Ser Ala Glu Glu Gly Lys Gln Ile Pro Asp Ser Leu
 1               5                  10                  15

Ser Thr Asp Leu
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Gly Arg Lys Lys Arg Arg Gln Arg Arg Pro Ser Arg Lys Leu
 1               5                  10                  15

Asn Thr Glu Ile
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys His Ser Arg Lys Ser Ser Ser Tyr Ser Ser Ser Thr Thr Val
 1               5                  10                  15

Lys Thr Ser Tyr
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Ser Asp Pro Glu Asn Glu Pro Phe Asp Glu Asp Gln His Thr Gln
 1               5                  10                  15

Ile Thr Lys Val
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 45

Ser Ala Thr Glu Ser Ala Glu Ser Ile Glu Ile Tyr Ile Pro Glu Ala
 1               5                  10                  15

Gln Thr Arg Leu
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Ser Tyr Val Arg Asp Asp Ala Ile Phe Ile Lys Ala Ile Val Asp
 1               5                  10                  15

Leu Thr Gly Leu
            20

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Trp Asp Asp Ser Ala Arg Ala Ala Gly Gly Gln Gly Leu His Val
 1               5                  10                  15

Thr Ala Leu

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Glu Leu Val Asp Arg Gly Glu Val Arg Gln Phe Thr Leu Arg His
 1               5                  10                  15

Trp Leu Lys Val
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Pro Thr Pro Thr Leu Gly Leu Asn Leu Gly Asn Asp Pro Asp Arg
 1               5                  10                  15

Gly Thr Ser Ile
            20

<210> SEQ ID NO 50
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Ser Asp Pro Glu Asn Glu Pro Phe Asp Glu Asp Gln His Thr Gln
 1               5                  10                  15

Ile Thr Lys Val
            20

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Lys Gly Thr Tyr Leu Thr Asp Glu Thr His Arg Glu Val Lys Phe
 1               5                  10                  15

Thr Ser Leu

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Asp Phe Arg Arg Ala Phe Arg Arg Ile Leu Ala Arg Pro Trp Thr
 1               5                  10                  15

Gln Thr Ala Trp
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Gly Thr Leu Leu Leu Glu Arg Val Ile Phe Pro Ser Val Lys Ile
 1               5                  10                  15

Ala Thr Leu Val
            20

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Asp Ser Arg Pro Ser Phe Val Gly Ser Ser Ser Gly His Thr Ser
 1               5                  10                  15

Thr Thr Leu
```

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Ala Ala Gly Phe Asn Ser Thr Gly Leu Pro His Ser Thr Thr
 1               5                  10                  15

Arg Val

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Arg Glu Asp Ile Tyr Val Asn Tyr Pro Thr Phe Ser Arg Arg Pro
 1               5                  10                  15

Lys Thr Arg Val
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Ser Trp Arg Arg Ser Ser Leu Ser Glu Ser Glu Asn Ala Thr Ser
 1               5                  10                  15

Leu Thr Thr Phe
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Ala Ser Lys Ser Ala Glu Glu Gly Lys Gln Ile Pro Asp Ser Leu
 1               5                  10                  15

Ser Thr Asp Leu
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Pro Ile Pro Ala Gly Gly Cys Thr Phe Ser Gly Ile Phe Pro Thr Leu
1               5                   10                  15

Thr Ser Pro Leu
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Thr Asp Tyr Leu Val Gln Pro Phe Met Asp Gln Leu Ala Phe His
1               5                   10                  15

Gln Phe Tyr Ile
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Gly Ser Ala Leu Gln Ala Trp Arg His Thr Ser Arg Gln Ala Thr
1               5                   10                  15

Glu Ser Thr Val
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Glu Asn Asp Tyr Glu Ser Ile Ser Asp Leu Gln Gln Gly Arg Asp
1               5                   10                  15

Ile Thr Arg Leu
            20

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ser Lys Ser Lys Ser Ser Glu Glu Ser Gln Thr Phe Phe Gly Leu
1               5                   10                  15

Tyr Lys Leu

<210> SEQ ID NO 64
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 64

Ala Val Gly Gly Arg Pro Ala Arg Gly Gly Arg Leu Gln Gly Arg Arg
 1               5                   10                  15

Gln Thr Gln Val
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Ala Gly Gly Arg Ser Ala Arg Gly Gly Arg Leu Gln Gly Arg Arg
 1               5                   10                  15

Glu Thr Ala Leu
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Pro Gly Ala Leu Asp Tyr Ala Ala Phe Ser Ser Ala Leu Tyr Gly
 1               5                   10                  15

Glu Ser Asp Leu
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Gln Gly Phe Pro Gly Pro Ala Thr Trp Arg Arg Ile Ser Ser Leu
 1               5                   10                  15

Glu Ser Glu Val
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Pro Ala Thr Pro Ser Pro Arg Leu Ala Leu Pro Ala His His Asn
 1               5                   10                  15

Ala Thr Arg Leu
            20
```

```
<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Trp Thr Gly Arg Ala Met Ser Ala Trp Lys Pro Thr Arg Arg
  1               5                  10                  15

Glu Thr Glu Val
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Gly Ala Val Arg Thr Pro Leu Ser Gln Val Asn Lys Val Trp Asp
  1               5                  10                  15

Gln Ser Ser Val
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Tyr Ser Glu Leu Asn Tyr Glu Thr Ser His Tyr Pro Ala Ser Pro
  1               5                  10                  15

Asp Ser Trp Val
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Ile Pro Ala Gly Gly Cys Thr Phe Ser Gly Ile Phe Pro Thr Leu
  1               5                  10                  15

Thr Ser Pro Leu
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73
```

```
Val His Asp Ala Glu Ser Ser Asp Glu Asp Gly Tyr Asp Trp Gly Pro
1               5                   10                  15

Ala Thr Asp Leu
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Asn Ser Cys Ser Asn Arg Arg Val Tyr Lys Lys Met Pro Ser Ile
1               5                   10                  15

Glu Ser Asp Val
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ala Thr Ser Arg Asn Gly His Ser Ala Arg Gln His Val Val Ala
1               5                   10                  15

Asp Thr Glu Leu
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Thr Met Pro Ala Ala Met Tyr Arg Leu Leu Thr Ala Gln Glu Gln
1               5                   10                  15

Pro Val Tyr Ile
            20

<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Thr Leu Leu Leu Thr Glu Asn Glu Gly Asp Lys Thr Glu Glu Gln
1               5                   10                  15

Val Ser Tyr Val
            20

<210> SEQ ID NO 78
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 78

His His Leu Val Ala Gln Arg Asp Ile Arg Gln Phe Gln Leu Gln His
 1               5                  10                  15

Trp Leu Ala Ile
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Thr Ser Asp Met Lys Asp Leu Val Gly Asn Ile Glu Gln Asn Glu
 1               5                  10                  15

His Ser Val Ile
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Gly Arg Lys Lys Arg Arg Gln Arg Arg Arg Lys Leu Ser Ser Ile
 1               5                  10                  15

Glu Ser Asp Val
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Gln Phe His Arg Gly Ser Arg Ala Gln Ser Phe Leu Gln Thr Glu
 1               5                  10                  15

Thr Ser Val Ile
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Ile Ser Pro Gly Gly Leu Glu Pro Pro Ser Glu Lys His Phe Arg
 1               5                  10                  15

Glu Thr Glu Val
            20
```

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Gly Arg Lys Lys Arg Arg Gln Arg Arg Pro Ser Arg Lys Leu
 1               5                  10                  15

Asn Thr Glu Ile
            20

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Thr Asn Asn Asn Pro Asn Ser Ala Val Asn Ile Lys Lys Ile Phe
 1               5                  10                  15

Thr Asp Val

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Pro Gln Ile Ala Ala Leu Lys Glu Glu Thr Glu Glu Glu Val Gln
 1               5                  10                  15

Asp Thr Arg Leu
            20

<210> SEQ ID NO 86
<211> LENGTH: 96
<212> TYPE: PRT
<213> ORGANISM: Homo sapiens

<400> SEQUENCE: 86

Leu Glu Tyr Glu Glu Ile Thr Leu Glu Arg Gly Asn Ser Gly Leu Gly
 1               5                  10                  15

Phe Ser Ile Ala Gly Gly Thr Asp Asn Pro His Ile Gly Asp Asp Pro
                20                  25                  30

Ser Ile Phe Ile Thr Lys Ile Ile Pro Gly Gly Ala Ala Ala Gln Asp
            35                  40                  45

Gly Arg Leu Arg Val Asn Asp Ser Ile Leu Phe Val Asn Glu Val Asp
        50                  55                  60

Val Arg Glu Val Thr His Ser Ala Ala Val Glu Ala Leu Lys Glu Ala
65                  70                  75                  80

Gly Ser Ile Val Arg Leu Tyr Val Met Arg Arg Lys Pro Pro Ala Glu
                85                  90                  95

<210> SEQ ID NO 87

```
<211> LENGTH: 107
<212> TYPE: PRT
<213> ORGANISM: Homo sapiens

<400> SEQUENCE: 87

Gly Ile His Val Met Arg Arg Lys Pro Ala Glu Lys Val Met Glu
1               5                   10                  15

Ile Lys Leu Ile Lys Gly Pro Lys Gly Leu Gly Phe Ser Ile Ala Gly
                20                  25                  30

Gly Val Gly Asn Gln His Ile Pro Gly Asp Asn Ser Ile Tyr Val Thr
            35                  40                  45

Lys Ile Ile Glu Gly Gly Ala His Lys Asp Gly Arg Leu Gln Ile
    50                  55                  60

Gly Asp Lys Ile Leu Ala Val Asn Ser Val Gly Leu Glu Asp Val Met
65                  70                  75                  80

His Glu Asp Ala Val Ala Leu Lys Asn Thr Tyr Asp Val Val Tyr
                85                  90                  95

Leu Lys Val Ala Lys Pro Ser Asn Ala Tyr Leu
                100                 105

<210> SEQ ID NO 88
<211> LENGTH: 120
<212> TYPE: PRT
<213> ORGANISM: Homo sapiens

<400> SEQUENCE: 88

Pro Val Ala Lys Asp Leu Leu Gly Glu Glu Asp Ile Pro Arg Glu Pro
1               5                   10                  15

Arg Arg Ile Val Ile His Arg Gly Ser Thr Gly Leu Gly Phe Asn Ile
                20                  25                  30

Val Gly Gly Glu Asp Gly Glu Gly Ile Phe Ile Ser Phe Ile Leu Ala
            35                  40                  45

Gly Gly Pro Ala Asp Leu Ser Gly Glu Leu Arg Lys Gly Asp Gln Ile
    50                  55                  60

Leu Ser Val Asn Gly Val Asp Leu Arg Asn Ala Ser His Glu Gln Ala
65                  70                  75                  80

Ala Ile Ala Leu Lys Asn Ala Gly Gln Thr Val Thr Ile Ile Ala Gln
                85                  90                  95

Tyr Lys Pro Glu Glu Tyr Ser Arg Phe Glu Ala Lys Ile His Asp Leu
                100                 105                 110

Arg Glu Gln Leu Met Asn Ser Ser
            115                 120

<210> SEQ ID NO 89
<211> LENGTH: 101
<212> TYPE: PRT
<213> ORGANISM: Homo sapiens

<400> SEQUENCE: 89

Pro Ser Glu Leu Lys Gly Lys Phe Ile His Thr Lys Leu Arg Lys Ser
1               5                   10                  15

Ser Arg Gly Phe Gly Phe Thr Val Val Gly Gly Asp Glu Pro Asp Glu
                20                  25                  30

Phe Leu Gln Ile Lys Ser Leu Val Leu Asp Gly Pro Ala Ala Leu Asp
            35                  40                  45

Gly Lys Met Glu Thr Gly Asp Val Ile Val Ser Val Asn Asp Thr Cys
    50                  55                  60
```

```
Val Leu Gly His Thr His Ala Gln Val Val Lys Ile Phe Gln Ser Ile
 65                  70                  75                  80

Pro Ile Gly Ala Ser Val Asp Leu Glu Leu Cys Arg Gly Tyr Pro Leu
             85                  90                  95

Pro Phe Asp Pro Asp
            100

<210> SEQ ID NO 90
<211> LENGTH: 103
<212> TYPE: PRT
<213> ORGANISM: Homo sapiens

<400> SEQUENCE: 90

Gln Arg Val Glu Ile His Lys Leu Arg Gln Gly Glu Asn Leu Ile Leu
 1               5                  10                  15

Gly Phe Ser Ile Gly Gly Gly Ile Asp Gln Asp Pro Ser Gln Asn Pro
             20                  25                  30

Phe Ser Glu Asp Lys Thr Asp Lys Gly Ile Tyr Val Thr Arg Val Ser
         35                  40                  45

Glu Gly Gly Pro Ala Glu Ile Ala Gly Leu Gln Ile Gly Asp Lys Ile
     50                  55                  60

Met Gln Val Asn Gly Trp Asp Met Thr Met Val Thr His Asp Gln Ala
 65                  70                  75                  80

Arg Lys Arg Leu Thr Lys Arg Ser Glu Glu Val Val Arg Leu Leu Val
             85                  90                  95

Thr Arg Gln Ser Leu Gln Lys
            100

<210> SEQ ID NO 91
<211> LENGTH: 20
<212> TYPE: PRT
<213> ORGANISM: Homo sapiens

<400> SEQUENCE: 91

Leu Asn Ser Ser Ser Asn Arg Arg Val Tyr Lys Lys Met Pro Ser Ile
 1               5                  10                  15

Glu Ser Asp Val
             20

<210> SEQ ID NO 92
<211> LENGTH: 22
<212> TYPE: PRT
<213> ORGANISM: Homo sapiens

<400> SEQUENCE: 92

Arg Arg Arg Ser Gly Leu Asp Asp Ile Asn Pro Thr Val Leu Leu Lys
 1               5                  10                  15

Glu Arg Ser Thr Glu Leu
             20

<210> SEQ ID NO 93
<211> LENGTH: 9
<212> TYPE: PRT
<213> ORGANISM: Homo sapiens

<400> SEQUENCE: 93

Ala Val Glu Arg Pro Ser Thr Glu Leu
 1               5

<210> SEQ ID NO 94
```

```
-continued

<211> LENGTH: 11
<212> TYPE: PRT
<213> ORGANISM: Homo sapiens

<400> SEQUENCE: 94

Tyr Gly Arg Lys Lys Arg Arg Gln Arg Arg Arg
 1               5                  10
```